(12) United States Patent
Kaslow et al.

(10) Patent No.: US 6,372,435 B1
(45) Date of Patent: Apr. 16, 2002

(54) METHODS OF SURVEYING FOR CC (BETA) CHEMOKINE RECEPTOR VARIANTS AND THEIR ASSOCIATION WITH HIV-1 TRANSMISSION AND/OR DISEASE PROGRESSION

(75) Inventors: Richard A. Kaslow; Jianming Tang, both of Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/638,509

(22) Filed: Aug. 11, 2000

Related U.S. Application Data

(60) Provisional application No. 60/148,530, filed on Aug. 12, 1999.

(51) Int. Cl.[7] ................................................. C12Q 1/68
(52) U.S. Cl. ............................... 435/6; 435/5; 435/91.1; 435/91.2; 514/329; 544/188; 544/193; 544/209; 544/214; 544/222; 544/223
(58) Field of Search ............................. 435/5, 6, 91.1, 435/91.2; 514/329; 544/188, 193, 209, 214, 222, 223

(56) References Cited

U.S. PATENT DOCUMENTS 6,136,827 A * 10/2000 Caldwell et al. ............. 514/329

* cited by examiner

Primary Examiner—W. Gary Jones
Assistant Examiner—Janell E. Taylor
(74) Attorney, Agent, or Firm—Benjamin Aaron Adler

(57) ABSTRACT

The present invention provides methods of correlating genetic variants in the beta-chemokine receptor 5 (CCR5) locus, more specifically CCR5 promoter alleles and genotypes, with HIV-1 transmission and/or disease progression in individuals and populations.

21 Claims, 19 Drawing Sheets

| | | | | | |
|---|---|---|---|---|---|
| P*0101: | $G_{59029}$ | $T_{59353}$—$C_{59356}$—$G_{59402}$ | $G_{59648}$—$C_{59653}$ | (=P4) | (SEQ ID No. 24) |
| P*0102: | $G_{59029}$ | $T_{59353}$—$C_{59356}$—$A_{59402}$ | $G_{59648}$—$C_{59653}$ | (=P2) | (SEQ ID No. 25) |
| P*0103: | $G_{59029}$ | $T_{59353}$—$T_{59356}$—$A_{59402}$ | $G_{59648}$—$C_{59653}$ | (=P3) | (SEQ ID No. 26) |
| P*0104: | $G_{59029}$ | $T_{59353}$—$C_{59356}$—$A_{59402}$ | $A_{59648}$—$C_{59653}$ | (=P2) | (SEQ ID No. 27) |
| P*0201: | $A_{59029}$ | $C_{59353}$—$C_{59356}$—$A_{59402}$ | $G_{59648}$—$C_{59653}$ | (=P1) | (SEQ ID No. 28) |
| P*0202: | $A_{59029}$ | $C_{59353}$—$C_{59356}$—$A_{59402}$ | $G_{59648}$—$T_{59653}$ | (=P1) | (SEQ ID No. 29) |

Fig. 1B

|  | SIE-like | TATA-like |
|---|---|---|
| Human | CCCGTAA | TTAAT |
| Chimpanzee | CCCATAA | TTAAT |
| Macaque | CCCGTGA | --AAT |
| Sooty mangabey | CCCGTGA | --AAT |

Fig. 5A

|        | P*0101 | P*0102 | P*0103 | P*0201 | P*0202 | Ptr   | Mne   | Cat   |
|--------|--------|--------|--------|--------|--------|-------|-------|-------|
| P*0101 | 0.000  |        |        |        |        |       |       |       |
| P*0102 | 0.001  | 0.000  |        |        |        |       |       |       |
| P*0103 | 0.002  | 0.001  | 0.000  |        |        |       |       |       |
| P*0201 | 0.003  | 0.002  | 0.003  | 0.000  |        |       |       |       |
| P*0202 | 0.004  | 0.003  | 0.004  | 0.001  | 0.000  |       |       |       |
| Ptr    | 0.010  | 0.009  | 0.010  | 0.011  | 0.012  | 0.000 |       |       |
| Mne    | 0.044  | 0.043  | 0.044  | 0.046  | 0.047  | 0.050 | 0.000 |       |
| Cat    | 0.046  | 0.045  | 0.046  | 0.047  | 0.048  | 0.052 | 0.020 | 0.000 |

Fig. 5B

P*0101  $G_{59029}-T_{59353}-C_{59356}-G_{59402}-C_{59653}$  (SEQ ID No. 19)
P*0102  $G_{59029}-T_{59353}-C_{59356}-A_{59402}-C_{59653}$  (SEQ ID No. 20)
P*0103  $G_{59029}-T_{59353}-T_{59356}-A_{59402}-C_{59653}$  (SEQ ID No. 21)
P*0201  $A_{59029}-C_{59353}-C_{59356}-A_{59402}-C_{59653}$  (SEQ ID No. 22)
P*0202  $A_{59029}-C_{59353}-C_{59356}-A_{59402}-T_{59653}$  (SEQ ID No. 23)

| CCR2 | CCR5 $P_U$ | | | CCR5 | | CCR5 $P_D$ | | CCR5 | |
|---|---|---|---|---|---|---|---|---|---|
| 64 | 29 | 208 | 303 | 627 | 630 | 676 | 927 | | |
| V | A | G | G | T | C | A | C | (*0102)[1] | WT = HHA[2] |
| V | A | T | A | T | C | A | C | (*0102) | WT = HHB (rare) |
| V | A | A | G | T | C | G | C | (*0101) | WT = HHC |
| V | A | A | G | T | T | A | C | (*0103) | WT = HHD (rare) |
| V | A | T | A | C | C | A | C | (*0201) | WT = HHE |
| V | A | G | A | C | C | A | T | (*0202) | WT = HHF*1 (rare) |
| I | A | G | A | C | C | A | T | (*0202) | WT = HHF*2 |
| V | G | G | A | C | C | A | C | (*0201) | WT = HHG*1 |
| V | G | G | A | C | C | A | C | (*0201) | Δ32 = HHG*2 |

* For any given haplotype the recombination rate is < 1%.

Fig. 9

Log₁₀ VL: Mean (SD) in Caucasians

|  | Visit 1 | Visit 2 | Visit 3 |
|---|---|---|---|
| HHA or HHB (n=28-42) | 4.40 (0.90) | 4.35 (0.75) | 4.29 (0.85) |
| HHC (n=94-126) | 4.41 (0.83) | 4.27 (0.72) | 4.34 (0.71) |
| HHE | 4.32 (0.87) | 4.33 (0.72) | 4.35 (0.70) |
| HHF*2 (n=98-144) | 4.16 (0.80) | 4.13 (0.68) | 4.22 (0.79) |
| HHG*1 (n=32-55) | 4.28 (0.89) | 4.10 (0.78) | 4.10 (0.62) |
| HHG*2 (Δ32) (n=29-42) | 4.25 (0.88) | 4.05 (0.81) | 4.12 (0.62) |
| (n=32-52) | | | |

Fig. 11A

Log$_{10}$ VL: Mean (SD) and Geometric Mean (GM) in Caucasians

| | Visit 1 | Visit 2 | Visit 3 |
|---|---|---|---|
| HHG*2/HHF*2 | 4.13 (0.90) | 3.34 (0.52) [1] | 3.12 (0.52) [1] |
| (n=4-8) GM = | 13,490 | 2,188 | 1,318 |
| HHG2 w/o HHF*2 | 4.28 (0.89) | 4.10 (0.79) [2] | 4.11 (0.61) [2] |
| (n=29-42) GM = | 19,055 | 12,589 | 12,882 |
| HHF*2 w/o HHG*2 | 4.17 (0.79) | 4.22 (0.64) | 4.37 (0.69) |
| (n=28-47) GM = | 14,791 | 16,596 | 23,442 |
| All others | 4.39 (0.84) | 4.38 (0.71) | 4.41 (0.71) |
| (n=126-174) GM = | 24,547 | 23,988 | 25,704 |

[1] VL differed at visits 2 and 3 ($P = 0.0008$ and $0.0002$, respectively)
[2] $P$ at visits 2 and 3 = $0.0342$ and $0.0405$, respectively.

Fig. 11B

Log$_{10}$ VL: Mean (SD) and Geometric Mean (GM) in Caucasians

|  | Visit 1 | Visit 2 | Visit 3 |
|---|---|---|---|
| HHG*2/HHF*2 | 4.13 (0.90) | 3.34 (0.52) | 3.12 (0.52) |
| (n=4-8) | GM = 13,490 | 2,188 | 1,318 |
| HHE/HHE | 4.43 (0.90) | 4.69 (0.46) [1] | 4.59 (0.43) [1] |
| (n=3-31) | GM = 26,915 | 48,978 | 38,904 |
| Others | 4.32 (0.84) | 4.26 (0.73) | 4.32 (0.72) |
| (n=74-232) | GM = 20,796 | 18,197 | 21,086 |

[1] HHE/HHE had the highest VL at visits 2 and 3 ($P = 0.007 - 0.1$).

Fig. 12

SEQUENCE LISTING

```
<160> NUMBER OF SEQ ID NOS: 35

<210> SEQ ID NO 1
<211> LENGTH: 18
<212> TYPE: DNA
<213> ORGANISM: Artificial Sequence
<220> FEATURE:
<221> NAME/KEY: primer_bind
<223> OTHER INFORMATION: universal M13 primer

<400> SEQUENCE: 1
acaggaaaca gctatgac                                                 18

<210> SEQ ID NO 2
<211> LENGTH: 18
<212> TYPE: DNA
<213> ORGANISM: Artificial Sequence
<220> FEATURE:
<221> NAME/KEY: primer_bind
<223> OTHER INFORMATION: CCR2b-5/1S, primer used for typing major
      polymorphism in CCR2b, CCR5 and the CCR5 downstream
      promoter region

<400> SEQUENCE: 2
tgggcaacat gctggtcg                                                 18

<210> SEQ ID NO 3
<211> LENGTH: 18
<212> TYPE: DNA
<213> ORGANISM: Artificial Sequence
<220> FEATURE:
<221> NAME/KEY: primer_bind
<223> OTHER INFORMATION: CCR2b-5/2S, primer used for typing major
      polymorphism in CCR2b, CCR5 and the CCR5 downstream
      promoter region

<400> SEQUENCE: 3
tgggcaacat gctggtca                                                 18

<210> SEQ ID NO 4
<211> LENGTH: 21
<212> TYPE: DNA
<213> ORGANISM: Artificial Sequence
<220> FEATURE:
<221> NAME/KEY: primer_bind
<223> OTHER INFORMATION: CCR2b-3/1G, primer used for typing major
      polymorphism in CCR2b, CCR5 and the CCR5 downstream
      promoter region

<400> SEQUENCE: 4
tggaaaataa gggccacaga c                                             21
```

```
<210> SEQ ID NO 5
<211> LENGTH: 18
<212> TYPE: DNA
<213> ORGANISM: Artificial Sequence
<220> FEATURE:
<221> NAME/KEY: primer_bind
<223> OTHER INFORMATION: CCR5P-5/1S, primer used for typing major
      polymorphism in CCR2b, CCR5 and the CCR5 downstream
      promoter region

<400> SEQUENCE: 5
gagtggagaa aaaggggg                                                 18

<210> SEQ ID NO 6
<211> LENGTH: 18
<212> TYPE: DNA
<213> ORGANISM: Artificial Sequence
<220> FEATURE:
<221> NAME/KEY: primer_bind
<223> OTHER INFORMATION: CCR5P-5/2S, primer used for typing major
      polymorphism in CCR2b, CCR5 and the CCR5 downstream
      promoter region

<400> SEQUENCE: 6
gagtggagaa aaagggga                                                 18

<210> SEQ ID NO 7
<211> LENGTH: 22
<212> TYPE: DNA
<213> ORGANISM: Artificial Sequence
<220> FEATURE:
<221> NAME/KEY: primer_bind
<223> OTHER INFORMATION: CCR5P-3/1S, primer used for typing major
      polymorphism in CCR2b, CCR5 and the CCR5 downstream
      promoter region

<400> SEQUENCE: 7
agaatagatc tctggtctga aa                                            22

<210> SEQ ID NO 8
<211> LENGTH: 22
<212> TYPE: DNA
<213> ORGANISM: Artificial Sequence
<220> FEATURE:
<221> NAME/KEY: primer_bind
<223> OTHER INFORMATION: CCR5P-3/2S, primer used for typing major
      polymorphism in CCR2b, CCR5 and the CCR5 downstream
      promoter region

<400> SEQUENCE: 8
agaatagatc tctggtctga ag                                            22

<210> SEQ ID NO 9
<211> LENGTH: 23
<212> TYPE: DNA
<213> ORGANISM: Artificial Sequence
<220> FEATURE:
<221> NAME/KEY: primer_bind
<223> OTHER INFORMATION: CCR5P-3/3S, primer used for typing major
      polymorphism in CCR2b, CCR5 and the CCR5 downstream
      promoter region

<400> SEQUENCE: 9
gagaatagat ctctggtcta aaa                                           23

<210> SEQ ID NO 10
<211> LENGTH: 22
<212> TYPE: DNA
<213> ORGANISM: Artificial Sequence
```

```
<220> FEATURE:
<221> NAME/KEY: primer_bind
<223> OTHER INFORMATION: CCR5P-3/4S, primer used for typing major
      polymorphism in CCR2b, CCR5 and the CCR5 downstream
      promoter region

<400> SEQUENCE: 10
tagagaatag atctctggtc tg                                          22

<210> SEQ ID NO 11
<211> LENGTH: 22
<212> TYPE: DNA
<213> ORGANISM: Artificial Sequence
<220> FEATURE:
<221> NAME/KEY: primer_bind
<223> OTHER INFORMATION: CCR5P-3/5S, primer used for typing major
      polymorphism in CCR2b, CCR5 and the CCR5 downstream
      promoter region

<400> SEQUENCE: 11
tagagaatag atctctggtc ta                                          22

<210> SEQ ID NO 12
<211> LENGTH: 22
<212> TYPE: DNA
<213> ORGANISM: Artificial Sequence
<220> FEATURE:
<221> NAME/KEY: primer_bind
<223> OTHER INFORMATION: CCR5P-3/6S, primer used for typing major
      polymorphism in CCR2b, CCR5 and the CCR5 downstream
      promoter region

<400> SEQUENCE: 12
agaatcagag aacagttctt cc                                          22

<210> SEQ ID NO 13
<211> LENGTH: 22
<212> TYPE: DNA
<213> ORGANISM: Artificial Sequence
<220> FEATURE:
<221> NAME/KEY: primer_bind
<223> OTHER INFORMATION: CCR5P-3/7S, primer used for typing major
      polymorphism in CCR2b, CCR5 and the CCR5 downstream
      promoter region

<400> SEQUENCE: 13
agaatcagag aacagttctt ct                                          22

<210> SEQ ID NO 14
<211> LENGTH: 19
<212> TYPE: DNA
<213> ORGANISM: Artificial Sequence
<220> FEATURE:
<221> NAME/KEY: primer_bind
<223> OTHER INFORMATION: CCR5P-5/3S, primer used for typing major
      polymorphism in CCR2b, CCR5 and the CCR5 downstream
      promoter region

<400> SEQUENCE: 14
caggaaaccc atagaagac                                              19

<210> SEQ ID NO 15
<211> LENGTH: 19
<212> TYPE: DNA
<213> ORGANISM: Artificial Sequence
<220> FEATURE:
<221> NAME/KEY: primer_bind
<223> OTHER INFORMATION: CCR5P-5/4S, primer used for typing major
      polymorphism in CCR2b, CCR5 and the CCR5 downstream
``` promoter region

<400> SEQUENCE: 15
caggaaaccc atagaagat                                                                19

<210> SEQ ID NO 16
<211> LENGTH: 19
<212> TYPE: DNA
<213> ORGANISM: Artificial Sequence
<220> FEATURE:
<221> NAME/KEY: primer_bind
<223> OTHER INFORMATION: CCR5P-3/8G, primer used for typing major
      polymorphism in CCR2b, CCR5 and the CCR5 downstream
      promoter region

<400> SEQUENCE: 16
gtgggcacat attcagaag                                                                19

<210> SEQ ID NO 17
<211> LENGTH: 20
<212> TYPE: DNA
<213> ORGANISM: Artificial Sequence
<220> FEATURE:
<221> NAME/KEY: primer_bind
<223> OTHER INFORMATION: CCR5-SP4G, primer used for typing major
      polymorphism in CCR2b, CCR5 and the CCR5 downstream
      promoter region

<400> SEQUENCE: 17
tcattacacc tgcagctctc                                                               20

<210> SEQ ID NO 18
<211> LENGTH: 19
<212> TYPE: DNA
<213> ORGANISM: Artificial Sequence
<220> FEATURE:
<221> NAME/KEY: primer_bind
<223> OTHER INFORMATION: CCR5-PM6G, primer used for typing major
      polymorphism in CCR2b, CCR5 and the CCR5 downstream
      promoter region

<400> SEQUENCE: 18
tggtgaagat aagcctcac                                                                19

<210> SEQ ID NO 19
<211> LENGTH: 5
<212> TYPE: DNA
<213> ORGANISM: Unknown
<220> FEATURE:
<221> NAME/KEY: allele
<223> OTHER INFORMATION: CCR5 promoter allele P*0101

<400> SEQUENCE: 19 gtcgc                                                                                5

<210> SEQ ID NO 20
<211> LENGTH: 5
<212> TYPE: DNA
<213> ORGANISM: Unknown
<220> FEATURE:
<221> NAME/KEY: allele
<223> OTHER INFORMATION: CCR5 promoter allele P*0102

<400> SEQUENCE: 20 gtcac                                                                                5

<210> SEQ ID NO 21

```
<211> LENGTH: 5
<212> TYPE: DNA
<213> ORGANISM: Unknown
<220> FEATURE:
<221> NAME/KEY: allele
<223> OTHER INFORMATION: CCR5 promoter allele P*0103

<400> SEQUENCE: 21 gttac                                                                    5

<210> SEQ ID NO 22
<211> LENGTH: 5
<212> TYPE: DNA
<213> ORGANISM: Unknown
<220> FEATURE:
<221> NAME/KEY: allele
<223> OTHER INFORMATION: CCR5 promoter allele P*0201

<400> SEQUENCE: 22 accac                                                                    5

<210> SEQ ID NO 23
<211> LENGTH: 5
<212> TYPE: DNA
<213> ORGANISM: Unknown
<220> FEATURE:
<221> NAME/KEY: allele
<223> OTHER INFORMATION: CCR5 promoter allele P*0202

<400> SEQUENCE: 23 accat                                                                    5

<210> SEQ ID NO 24
<211> LENGTH: 6
<212> TYPE: DNA
<213> ORGANISM: Unknown
<220> FEATURE:
<221> NAME/KEY: allele
<223> OTHER INFORMATION: CCR5 promoter allele P*0101

<400> SEQUENCE: 24 gtcggc                                                                   6

<210> SEQ ID NO 25
<211> LENGTH: 6
<212> TYPE: DNA
<213> ORGANISM: Unknown
<220> FEATURE:
<221> NAME/KEY: allele
<223> OTHER INFORMATION: CCR5 promoter allele P*0102

<400> SEQUENCE: 25 gtcagc                                                                   6

<210> SEQ ID NO 26
<211> LENGTH: 6
<212> TYPE: DNA
<213> ORGANISM: Unknown
<220> FEATURE:
<221> NAME/KEY: allele
<223> OTHER INFORMATION: CCR5 promoter allele P*0103

<400> SEQUENCE: 26 gttagc                                                                   6

<210> SEQ ID NO 27
<211> LENGTH: 6
```

```
<212> TYPE: DNA
<213> ORGANISM: Unknown
<220> FEATURE:
<221> NAME/KEY: allele
<223> OTHER INFORMATION: CCR5 promoter allele P*0104

<400> SEQUENCE: 27 gtcaac                                                                    6

<210> SEQ ID NO 28
<211> LENGTH: 6
<212> TYPE: DNA
<213> ORGANISM: Unknown
<220> FEATURE:
<221> NAME/KEY: allele
<223> OTHER INFORMATION: CCR5 promoter allele P*0201

<400> SEQUENCE: 28 accagc                                                                    6

<210> SEQ ID NO 29
<211> LENGTH: 6
<212> TYPE: DNA
<213> ORGANISM: Unknown
<220> FEATURE:
<221> NAME/KEY: allele
<223> OTHER INFORMATION: CCR5 promoter allele P*0202

<400> SEQUENCE: 29 accagt                                                                    6

<210> SEQ ID NO 30
<211> LENGTH: 24
<212> TYPE: DNA
<213> ORGANISM: Artificial Sequence
<220> FEATURE:
<221> NAME/KEY: primer_bind
<223> OTHER INFORMATION:

<400> SEQUENCE: 30
gatagattat atctggagtg aaga                                               24

<210> SEQ ID NO 31
<211> LENGTH: 23
<212> TYPE: DNA
<213> ORGANISM: Artificial Sequence
<220> FEATURE:
<221> NAME/KEY: primer_bind
<223> OTHER INFORMATION:

<400> SEQUENCE: 31
atagattata tctggagtga agg                                                23

<210> SEQ ID NO 32
<211> LENGTH: 22
<212> TYPE: DNA
<213> ORGANISM: Artificial Sequence
<220> FEATURE:
<221> NAME/KEY: primer_bind
<223> OTHER INFORMATION:

<400> SEQUENCE: 32
aaagtctggt ctctagataa ga                                                 22

<210> SEQ ID NO 33
<211> LENGTH: 22
<212> TYPE: DNA
```

```
<213> ORGANISM: Artificial Sequence
<220> FEATURE:
<221> NAME/KEY: primer_bind
<223> OTHER INFORMATION:

<400> SEQUENCE: 33
gaagtctggt ctctagataa ga                                          22

<210> SEQ ID NO 34
<211> LENGTH: 25
<212> TYPE: DNA
<213> ORGANISM: Artificial Sequence
<220> FEATURE:
<221> NAME/KEY: primer_bind
<223> OTHER INFORMATION:

<400> SEQUENCE: 34
ttaaaactct ttagacaaca ggttt                                       25

<210> SEQ ID NO 35
<211> LENGTH: 24
<212> TYPE: DNA
<213> ORGANISM: Artificial Sequence
<220> FEATURE:
<221> NAME/KEY: primer_bind
<223> OTHER INFORMATION:

<400> SEQUENCE: 35
taaaactctt tagacaacag gttg                                        24
```

METHODS OF SURVEYING FOR CC (BETA) CHEMOKINE RECEPTOR VARIANTS AND THEIR ASSOCIATION WITH HIV-1 TRANSMISSION AND/OR DISEASE PROGRESSION

CROSS-REFERENCE TO RELATED APPLICATION

This non-provisional patent application claims benefit of provisional patent application U.S. Ser. No. 60/148,530 filed Aug. 12, 1999, now abandoned.

FEDERAL FUNDING LEGEND

This invention was produced in part using funds obtained through grants AI41951, AI40591 and AI42454 from NIAID, and grant DA04347 from NIDA. Consequently, the federal government has certain rights in this invention.

BACKGROUND OF THE INVENTION

1. Field of the Invention

The present invention relates generally to genotyping CCR alleles in individuals and populations. More specifically, the present invention relates to methods of correlating CCR alleles and/or genotypes, specifically CCR5 promoter alleles, with HIV-1 transmission and/or disease progression.

2. Description of the Related Art

"Chemokine" describes a closely related family of '*chemotactic cytokines*' with conserved sequences, known to be potent attractors for various leukocyte subsets such as neutrophils, monocytes, or lymphocytes. Chemokines are a large superfamily consisting of four subfamilies that display between two and four highly conserved $NH_2$-terminal cysteine amino acid residues. The CXC (or α) family has the first two $NH_2$-terminal cysteines separated by one nonconserved amino acid residue. In contrast, the CC (or β) family has these cysteines in juxtaposition, and the C (or γ) family has one lone $NH_2$-terminal cysteine residue, while the $CX_3C$ (or δ) family has these cysteines separated by three intervening amino acids. The large number of chemokines and their receptors, together with the expression of chemokine receptors on cells other than leukocytes (such as epithelial, endothelial and smooth muscle cells) is indicative of the importance of these molecules.

Six receptors for the CC family of chemokines have been identified: CC-CCR1, CC-CCR2, CC-CCR3, CC-CCR4, CC-CCR5 and the duffy blood group antigen. These proteins are seven transmembrane domain G protein-coupled receptors. In general, there is broad overlap in the ligands bound by the CC chemokine receptors. The human CCR5 and CCR2 chemokine receptor genes, which serve as co-receptors with CD4 for HIV, are tightly linked on chromosome 3p21–22, separated by 20 kb.

The complex mechanisms for HIV-1 entry into human $CD4^+$ cells reflect in part its evolving usage of co-receptors (35). For example, macrophage-tropic HIV-1 isolates infect cells by binding to the $CD4^+$ receptor and the CCR5 co-receptor (36), while T-cell-tropic viruses mainly use CXCR4 as the co-receptor (37). HIV-1 represents a close relative of simian immunodeficiency virus (SIV) that is naturally found in African primates, including chimpanzees and sooty mangabeys (15). Recent studies have confirmed that HIV-1 originated in the chimpanzee subspecies Pan troglodytes troglodytes from Central West Africa (16). Both HIV and SIV prefer CCR5 as their co-receptor for penetrating $CD4^+$ cells (17–19), which suggests that CCR5 is commonly expressed in both human and non-human primates. Therefore, highly conserved transcription factor binding elements may represent a critical mechanism for regulating transcription of the CCR5 gene, and may serve as appropriate targets for intervention experiments. Additionally, other members of the CCR co-receptor gene family also facilitate viral transmission (38), but they appear to have more restricted cellular distribution (19,39–40).

Recent work in AIDS cohorts has revealed associations between several polymorphisms in the CC (beta) chemokine receptor loci and either variable degrees of protection against HIV-1 transmission or variable evolution of the AIDS that follows (1–4). In Caucasians, homozygosity for a 32-bp deletion (Δ32) mutation in the CCR5 coding sequence leads to the absence of cell surface expression of CCR5, which confers nearly complete resistance to HIV-1 infection (1,41–44). Another less frequent mutation at nucleotide position 303 of the CCR5 coding sequence (m303) introduces a premature stop codon that also abolishes surface expression of CCR5 in Caucasians. Accordingly, an individual carrying both CCR5-Δ32 and m303 is resistant to HIV-1 infection (45). Carriage of a single copy of CCR5-Δ32 in the presence of CCR5 wild-type provides little if any resistance to HIV-1 infection, but does tend to delay the progression of disease (1,4,46), possibly through interference with translocation of the wild-type product (47). Neither the CCR5-Δ32 nor the CCR5-m303 allele is frequent in African and Asian populations (1,43,48). However, African and Asian ethnic groups also show great variability in acquisition and progression of the disease. Population-specific polymorphisms within the CCR5 gene may exist (49), but none of these have been associated with varying degrees of viral susceptibility (48). The use of CCR5 as the co-receptor is not altered whether or not additional CCR5 polymorphisms are present, regardless of the HIV-1 subtype (50).

In addition, extensive heterogeneities have been described in the expression and splicing of CCR5, apparently regulated by different CCR5 promoter alleles (3). More importantly, 2 CCR5 promoter variants have been associated with contrasting rates of HIV-1 disease progression (5,6). Expression of cell surface CCR5 also varies widely, even in individuals homozygous for wild type CCR5 (51,52), indicating differential regulation of CCR5 production. Therefore, variability in infectivity of primary HIV-1 isolates that prefer CCR5 as the co-receptor is observed even in wild type individuals. Detailed study of the organization of the CCR5 gene and its promoter has uncovered extensive heterogeneity in the 5' untranslated region (UTR) of CCR5 mRNA (13). Some of these polymorphisms may be linked to changes in splicing and may account for continuing uncertainties about the intron and exon boundaries (13–14,53). One CCR5 promoter variant (59653T) shows strong linkage disequilibrium with CCR2b-64I (2)—a CCR variant previously associated with retarded disease progression (4), and subsequent work has further detailed the relationships of CCR5 promoter markers to both CCR2b and CCR5-Δ32 (3,5,6). More recent association of the 59029G/G genotype with reduced promoter activity (5) also suggests that CCR5 promoter polymorphisms independently modulate HIV-1 disease progression.

The mechanisms and credibility of these specific genetic associations are under debate (3,10), especially because some of the CCR variants are tightly linked to each other (2). However, these findings highlight the importance of host genetic factors in HIV/AIDS and may guide development of new measures for the prevention and control of HIV-1-related diseases (7–9).

Polymorphisms at the CCR2b, CCR5, and CCR5 promoter loci have been analyzed in four ethnic groups, with a special emphasis on the relationships of CCR5 promoter allelic variants to other well-characterized markers previously associated with different outcomes of HIV-1 transmission and disease progression. In addition, the same CCR5 promoter polymorphisms were analyzed in HIV-1-infected Rwandan women, with a special emphasis on the influence of the genetic polymorphisms on HIV-1 disease progression.

The prior art is deficient in methods used to predict the likelihood and/or probability of HIV-1 transmission and/or disease progression based upon CCR alleles and/or genotypes. The present invention fulfills a long-standing need for the development of a rapid and informative genotyping strategy that can be readily applied to analyze CCR2, CCR5 and related genetic variants and to evaluate the relationship of each genotype to HIV transmission and disease progression.

SUMMARY OF THE INVENTION

Variability in HIV-1 infection has been associated with genetic variants in the beta-chemokine receptor 5 (CCR5) locus. Genetic variations (a 32-bp deletion and a point mutation) in the coding sequence of the HIV-1 co-receptor, CCR5, have been shown to confer resistance to HIV-1 infection by depleting CCR5 expression on the cell surface. While CCR5 coding sequences have exhibited relatively limited variation, its promoter sequence appears polymorphic in all major populations.

The studies reported herein revealed five major CCR5 promoter alleles with distributions that differed widely among the four distinct ethnic groups examined. Herein, the methods of the instant invention are used to present evidence that particular genetic variants of the CCR5 promoter appear to determine the infectability of an individual (i.e., herein, of heterosexual women in Kigali, Rwanda, and injecting drug users in New York, USA). Additionally, the present methods have been used to examine the relationship between the major CCR5 promoter genotypes and HIV-1 to AIDS disease progression (i.e., among 201 HIV-1-infected Rwandan women). The effects of disease progression-related CCR2b and CCR5 polymorphisms on early HIV-1 viral load were also determined in a cohort of homosexual HIV-1 seroconverters. The methods of the present invention allowed the inventors to establish an independent and strong linkage between HIV-1 transmission and CCR5 promoter alleles using these distinct cohorts and further, to validate the methodology of the present invention.

One object of the present invention is to provide methods of correlating CCR alleles and/or genotypes, specifically CCR5 promoter alleles, with HIV-1 transmission and/or disease progression.

In an embodiment of the present invention, there is provided a method of surveying CCR genotypes in a population, comprising the steps of: (a) obtaining biological samples from a representative number of individuals in a population, with each sample being from a different individual, wherein the sample contains genomic DNA; (b) combining a portion of each sample with at least one experimental primer combination and a control primer combination, thereby producing primer-annealed DNA, wherein the experimental primer combinations are selected from the group consisting of SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein the control primer combination is SEQ ID Nos. 17 & 18; (c) amplifying the primer-annealed DNA in a reaction, thereby producing amplicons, wherein reaction conditions for the amplification are optimized for sequence-specific amplification, wherein each experimental primer combination and the control primer combination are predicted to produce one or more amplicons having expected sizes in basepairs; (d) separating the amplicons by size, wherein the presence of: a 197 bp amplicon with the control primer combination is indicative of a CCR5 wildtype coding sequence; a 165 bp amplicon with the control primer combination is indicative of a CCR5-Δ32 coding sequence; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12 and a 309 bp amplicon with experimental primer combination SEQ ID Nos. 14 & 16 is indicative of a P*0101 CCR5 promoter allele; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13 and a 309 bp amplicon with experimental primer combination SEQ ID Nos. 14 & 16 is indicative of a P*0102 CCR5 promoter allele; a 363 bp amplicon with experimental primer combination SEQ ID Nos. 5 & 7, a 363 bp amplicon with experimental primer combination SEQ ID Nos. 5 & 9, a 367 bp amplicon with experimental primer combination SEQ ID Nos. 5 & 11, a 412 bp amplicon with experimental primer combination SEQ ID Nos. 5 & 13 and a 309 bp amplicon with experimental primer combination SEQ ID Nos. 14 & 16 is indicative of a P*0103 CCR5 promoter allele; a 363 b p amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a P*0201 CCR5 promoter allele; a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 15 & 16 is indicative of a P*0202 CCR5 promoter allele; (e) determining a CCR genotype for each sample based upon the CCR alleles indicated following step (d); and (f) compiling the genotypes determined in step (e), thereby genotyping the representative number of individuals in the population, thereby surveying CCR genotypes in the population.

In another embodiment of the present invention, there is provided a method of surveying HIV-1 co-receptor CCR alleles in an individual, comprising the steps of: (a) obtaining a biological sample from an individual, wherein the sample comprises genomic DNA; (b) combining a portion of the sample with at least one experimental primer combination and a control primer combination, thereby producing primer-annealed DNA, wherein the experimental primer combinations are selected from the group consisting of SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein the control primer combination is SEQ ID Nos. 17 & 18; (c) amplifying the primer-annealed DNA in a reaction, thereby producing amplicons, wherein reaction conditions for the amplification are optimized for sequence-specific amplification, wherein each experimental primer combination and the control primer combination are predicted to produce one or more amplicons having expected sizes in basepairs; and (d) separating the amplicons by size, wherein the presence of: a 197 bp amplicon with the control primer combination is indicative of a CCR5 wildtype coding sequence; a 165 bp amplicon with the control primer combination is indicative of a CCR5-Δ32 coding sequence; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12 and a 309 bp amplicon with experimental primer combination SEQ ID Nos. 14 & 16 is indicative of a P*0101 CCR5 promoter allele; a 363 bp amplicon with experimental primer combination SEQ ID Nos. 5 & 7, a 367 bp amplicon with experimental primer combination SEQ ID Nos. 5 & 10, a 412 b p amplicon with experimental primer combination SEQ ID Nos. 5 & 13 and a 309 bp amplicon with experimental primer combination SEQ ID Nos. 14 & 16 is indicative of a P*0102 CCR5 promoter allele; a 363 bp amplicon with experimental primer combination SEQ ID Nos. 5 & 7, a 363 bp amplicon with experimental primer combination SEQ ID Nos. 5 & 9, a 367 bp amplicon with experimental primer combination SEQ ID Nos. 5 & 11, a 412 bp amplicon with experimental primer combination SEQ ID Nos. 5 & 13 and a 309 bp amplicon with experimental primer combination SEQ ID Nos. 14 & 16 is indicative of a P*0103 CCR5 promoter allele; a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a P*0201 CCR5 promoter allele; a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 15 & 16 is indicative of a P*0202 CCR5 promoter allele.

In yet another embodiment of the present invention, there is provided a method of predicting the disease progression to AIDS in an HIV-1-infected individual, comprising the steps of: (a) obtaining a biological sample from an individual, wherein the sample comprises genomic DNA; (b) combining a portion of the sample with at least one experimental primer combination and a control primer combination, thereby producing primer-annealed DNA, wherein the experimental primer combinations are selected from the group consisting of SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein the control primer combination is SEQ ID Nos. 17 & 18; (c) amplifying the primer-annealed DNA in a reaction, thereby producing amplicons, wherein reaction conditions for the amplification are optimized for sequence-specific amplification, wherein each experimental primer combination and the control primer combination are predicted to produce one or more amplicons having expected sizes in basepairs; (d) separating the amplicons by size, wherein the presence of: a 363 bp amplicon with experimental primer combination SEQ ID Nos. 6 & 8, a 412 bp amplicon with experimental primer combination SEQ ID Nos. 6 & 13 and a 309 b p amplicon with experimental primer combination SEQ ID Nos. 14 & 16 is indicative of a CCR5 promoter genotype of P*0201/P*0201; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13, a 363 bp amplicon with experimental primer combination SEQ ID Nos. 6 & 8, a 412 b p amplicon with experimental primer combination SEQ ID Nos. 6 & 13, a 309 bp amplicon with experimental primer combination SEQ ID Nos. 14 & 16 and a 309 bp amplicon with experimental primer combination SEQ ID Nos. 15 & 16 is indicative of a CCR5 promoter genotype of P*0102/P*0202; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12, a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a CCR5 promoter genotype of P*0101/P*0201; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12, a 363 bp amplicon with experimental primer combination SEQ ID Nos. 6 & 8, a 412 bp amplicon with experimental primer combination SEQ ID Nos. 6 & 13, a 309 bp amplicon with experimental primer combination SEQ ID Nos. 14 & 16 and a 309 bp amplicon with experimental primer combination SEQ ID Nos. 15 & 16 is indicative of a CCR5 promoter genotype of P*0101/P*0202; wherein a CCR5 promoter genotype of P*0201/P*0201 or P*0102/P*0202 is predictive of an accelerated rate of AIDS progression in the individual (relative to an individual who does not possess the P*0201/P*0201 or P*0102/P*0202 gentoype), wherein a CCR5 promoter genotype of P*0101/P*0201 or P*0101/P*0202 is predictive of a slower rate of AIDS progression in the individual (relative to an individual who does not possess the P*0101/P*0201 or P*0101/P*0202 gentoype).

In still yet another embodiment of the present invention, there is provided a method of predicting the probability of HIV-1 infection in an individual, comprising the steps of: (a) obtaining a biological sample from an individual, wherein the sample comprises genomic DNA; (b) combining a portion of the sample with at least one experimental primer combination and a control primer combination, thereby producing primer-annealed DNA, wherein the experimental primer combinations are selected from the group consisting of SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein the control primer combination is SEQ ID Nos. 17 & 18; (c) amplifying the primer-annealed DNA in a reaction, thereby producing amplicons, wherein reaction conditions for the amplification are optimized for sequence-specific amplification, wherein each experimental primer combination and the control primer combination are predicted to produce one or more amplicons having expected sizes in basepairs; and (d) separating the amplicons by size, wherein the presence of: a 363 bp with experimental primer combination SEQ ID Nos. 6 & 8, a 412 bp with experimental primer combination SEQ ID Nos. 6 & 13 and a 309 bp with experimental primer combination SEQ ID Nos. 14 & 16 is indicative of a CCR5 promoter genotype of P*0201/P*0201; a 363 bp with experimental primer combination SEQ ID Nos. 5 & 7, a 367 bp with experimental primer combination SEQ ID Nos. 5 & 10, a 412 bp with experimental primer combination SEQ ID Nos. 5 & 12 and a 309 bp with experimental primer combination SEQ ID Nos. 14 & 16 is indicative of a CCR5 promoter genotype of P*0101/P*0101; wherein a CCR5 promoter genotype of P*0201/P*0201 is predictive of a decreased probability of HIV-1 infection in the individual (relative to an individual who does not possess the P*0201/P*0201 genotype), wherein a CCR5 promoter genotype of P*0101/P*0101 is predictive of an increased probability of HIV-1 infection in the individual (relative to an individual who does not possess the P*0101/P*0101 genotype).

In yet another embodiment of the present invention, there is provided a method of correlating CCR genotypes with HIV-1 transmission and/or disease progression, comprising the steps of: (a) obtaining biological samples from a representative number of individuals, wherein each sample is from a different individual, wherein the sample comprises genomic DNA; (b) assessing each individual's HIV-1 status and/or risk of acquiring HIV-1; (c) assigning each individual to a risk group, wherein the assignment is based upon the individual's HIV-1 status and/or risk of acquiring HIV-1; (d) combining a portion of each sample with at least one experimental primer combination and a control primer combination, thereby producing primer-annealed DNA, wherein the experimental primer combinations are selected from the group consisting of SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein the control primer combination is SEQ ID Nos. 17 & 18; (e) amplifying the primer-annealed DNA in a reaction, thereby producing amplicons, wherein reaction conditions for the amplification are optimized for sequence-specific amplification, wherein each experimental primer combination and the control primer combination are predicted to produce one or more amplicons having expected sizes in basepairs; and (f) separating the amplicons by size, wherein the presence of: a 197 bp amplicon with the control primer combination is indicative of a CCR5 wildtype coding sequence; a 165 bp amplicon with the control primer combination is indicative of a CCR5-Δ32 coding sequence; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12 and a 309 bp amplicon with experimental primer combination SEQ ID Nos. 14 & 16 is indicative of a P*0101 CCR5 promoter allele; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13 and a 309 bp amplicon with experimental primer combination SEQ ID Nos. 14 & 16 is indicative of a P*0102 CCR5 promoter allele; a 363 b p amplicon with experimental primer combination SEQ ID Nos. 5 & 7, a 363 bp amplicon with experimental primer combination SEQ ID Nos. 5 & 9, a 367 bp amplicon with experimental primer combination SEQ ID Nos. 5 & 11, a 412 bp amplicon with experimental primer combination SEQ ID Nos. 5 & 13 and a 309 bp amplicon with experimental primer combination SEQ ID Nos. 14 & 16 is indicative of a P*0103 CCR5 promoter allele; a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a P*0201 CCR5 promoter allele; a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 15 & 16 is indicative of a P*0202 CCR5 promoter allele.

In a further embodiment of the present invention, there is provided an oligonucleotide selected from the group consisting of SEQ ID Nos. 2–16. Other aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. The appended drawings illustrate preferred embodiments of the invention and should not be considered to limit the scope of the invention.

FIG. 1 shows a genetic map of CCR variants on chromosome 3 and the genotyping strategy of the present invention. FIG. 1B shows polymorphisms within and slightly beyond the boundaries of the CCR5 promoter. These polymorphisms define 6 allelic variants in these cohorts (P*0104 was only observed once in the 69 sequenced samples). Single polymorphic positions (59029 and 59653) and segments (boxed) in this region have been targeted in various studies and the corresponding alternative allele nomenclature is also shown (boxed).

FIG. 5 shows the phylogenetic relationships among CCR5 promoter sequences from humans (1–5; and see FIG. 6), chimpanzees (6), pig-tailed macaques (7), and sooty mangabeys (8). FIG. 5A shows CCR5 promoter sequences from non-human primate species demonstrate nucleotide substitutions in 2 putative transcription-factor-binding (TFB) elements: SIE-like (sis/platelet-derived growth factor-inducible element-like) and TATA-like (TATA box-like AT-rich sequence). FIG. 5B shows pair-wise genetic distance matrix calculated using Kimura's two-parameter method (31). The alleles from non-human primates (GenBank accession numbers AF109384, AF115963, AF115964) are identical to human allele P*0102 at all 5 positions found to be polymorphic in humans.

FIG. 6 shows the major CCR5 promoter alleles from humans (1–5) and their reported and predicted relationship to HIV-1 disease progression.

FIG. 9 shows nucleotides at polymorphic sites of stable CCR (CCR2-CCR5) haplotypes.

FIG. 10 shows HIV-1 viral load (VL) in people with different genotypes.

FIG. 11 shows HIV-1 viral load according to CCR haplotypes.

FIG. 12 shows the CCR genotypes exhibiting the most contrasting associations with viral load.

DETAILED DESCRIPTION OF THE INVENTION

Figure 1A:
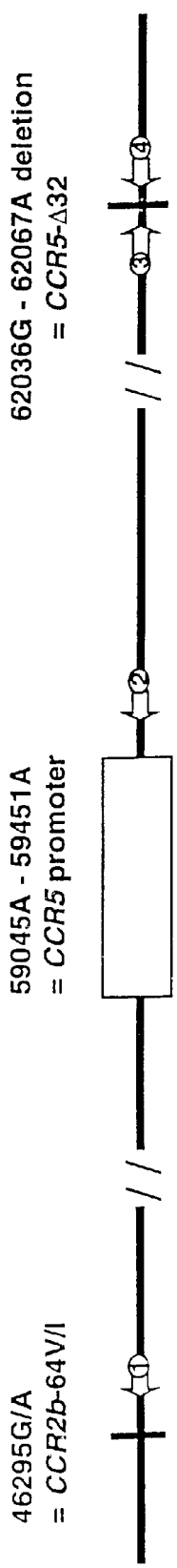
FIG. 1A shows polymorphisms in the coding region of CCR2b and CCR5, known as 64V/I and CCR5Δ32, respectively, occur at nucleotide positions 46295 (based upon GenBank sequence U95626) and from 62036 to 62067, respectively. Nucleotides 59052G and 59530C enclose the region associated with basal and induced CCR5 promoter activities.
Figure 1C:
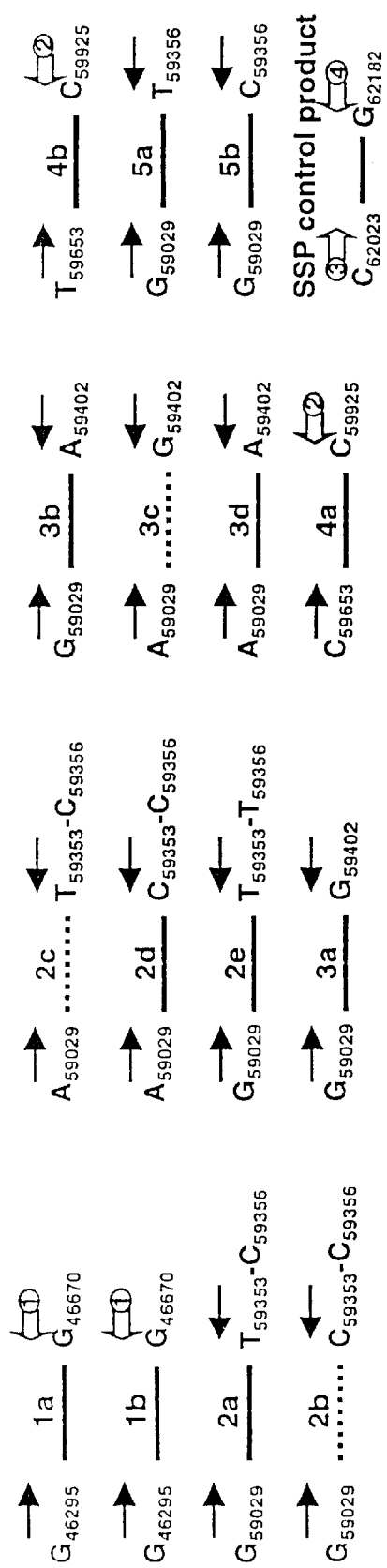
FIG. 1C shows that based upon the various features outlined above, genotyping can b e performed utilizing sequence-specific primers (PCR-SSP-based typing) that simultaneously target all major variants in 15 different PCR reactions. The polarity (5'→3') and the 3' terminal sequence of each sequence-specific and general primer used in PCR-SSP are indicated by solid and open arrows, respectively. Three SSP reactions (2b, 2c and 3c, as indicated by broken lines) do not contribute to allele assignment but have the potential to detect new alleles involving the targeted polymorphic sites. The control product in all reactions carries the 32 bp deleted region in the CCR5 coding sequence.

Variability in the natural history of HIV-1 infection has been associated with polymorphic genetic variants in the beta-chemokine receptor 5 (CCR5) locus. For instance, genetic variations in the HIV-1 co-receptor, CCR5, including a 32-bp deletion and a point mutation, have been shown to confer resistance to HIV-1 infection by depleting CCR5 expression on the cell surface. The studies reported herein reveal five major CCR5 promoter alleles with distributions that differed widely among the four distinct ethnic groups examined. Herein, evidence is presented that genetic variants of the CCR5 promoter also appear to determine the infectability of heterosexual women in Kigali, Rwanda, and injecting drug users in New York, USA. Additionally, the relationship of the major CCR5 promoter genotypes with HIV-1 disease progression has been examined among 201 HIV-1-infected Rwandan women. The effects of disease progression-related CCR2b and CCR5 polymorphisms on early HIV-1 viral load were also determined in a cohort of homosexual HIV-1 seroconverters.

In particular, promoter allele P*0103 ($G_{59029}$-$T_{59353}$-$T_{59356}$-$A_{59402}$-$C_{59653}$, SEQ ID No. 21) was largely restricted to blacks. The promoter allele P*0202 ($A_{59029}$-$C_{59353}$-$C_{59356}$-$A_{59402}$-$T_{59653}$, SEQ ID No. 23) was tightly linked to the slightly less frequent CCR2b-64I, a variant of the CCR2b gene which is about 12.7 kb upstream of the promoter region. Another closely related promoter allele P*0201 ($A_{59029}$-$C_{59353}$-$C_{59356}$-$A_{59402}$-$C_{59653}$, SEQ ID No. 22) exclusively carried the far less common CCR5-Δ32, a 32-bp deletion in the CCR5 coding sequence 2 kb downstream from the promoter. Among human, chimpanzee, pig-tailed macaque, and sooty mangabey promoter allelic sequences, the apparent ancestral lineage of the promoter sequence ($G_{59029}$-$T_{59353}$-$C_{59356}$-$A_{59402}$-$C_{59653}$=human P*0102, SEQ ID No. 20) was highly conserved across the primate species analyzed here, while P*0201 and P*0202 arose more recently than the other 3 major alleles.

Among the various CCR5 promoter genotypes comprising the five major alleles (P*0101, P*0102, P*0103, P*0201, and P*0202), the genotypes involving allele P*0201 were associated with protection against HIV-1 infection (OR=0.4, p<0.001 in Kigali; OR=0.5, p=0.012 in New York), while the homozygous genotype P*0101/*0101 showed the opposite effect (OR=4.7, p=0.140 in Kigali; OR=4.1, p=0.002 in New York). According to multivariate logistic regression models, these observed promoter effects were independent of age, ethnicity and at least seven high-risk behavioral factors known to influence HIV-1 infection in the two cities: in Kigli, HIV-1 infection=6.21+0.68×(risk score)−0.13×age−0.79×(CCR5 promoter genotypes involving P*0201); in New York, HIV-1 infection=1.60+0.31× (needle sharing)−0.06×age+1.41×(CCR5 promoter genotype P*0101/*0101)−0.83×(being Caucasian). Differences in the adjusted genetic effects between the two cohorts reflected differences in the distribution of the two mutually exclusive promoter alleles involved.

Two promoter genotypes (designated P*0201/*0201 and P*0102/*0202) were weakiy associated with accelerated HIV-1 disease progression (p=0.072 and 0.058, respectively). In contrast, 2 promoter genotypes involving a common allele P*0101 (P*0101/*0201 and P*0101/*0202) were collectively associated with slower disease progression (p=0.001, pc=0.015). Both P*0102/*0202 and P*0101/*0202 genotypes always carried CCR2b-64I, but CCR2b-64I alone had no detectable effect on disease progression. These findings support and refine some of the earlier observations regarding CCR5 promoter polymorphisms and futher suggest that the previously recognized CCR2b-64I relationship is secondary to the CCR5 promoter allelic effects. Thus, the present invention establishes an independent linkage between HIV-1 transmission and the genetic variation within the CCR5 promoter alleles and further establishes a mechanism by which CCR chemokine receptor polymorphisms governs the initiation and pathogenesis of HIV-1 infection.

The present invention is directed towards methods of correlating CCR alleles and/or genotypes, specifically CCR5 promoter alleles, with HIV-1 transmission and/or disease progression in an individual or population.

The present invention is directed towards a method of surveying CCR genotypes in a population, comprising the steps of: (a) obtaining biological samples from a representative number of individuals in a population, wherein each sample is from a different individual, wherein the sample comprises genomic DNA; (b) combining a portion of each sample with at least one experimental primer combination and a control primer combination, thereby producing primer-annealed DNA, wherein the experimental primer combinations are selected from the group consisting of SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein the control primer combination is SEQ ID Nos. 17 & 18; (c) amplifying the primer-annealed DNA in a reaction, thereby producing amplicons, wherein reaction conditions for the amplification are optimized for sequence-specific amplification, wherein each experimental primer combination and the control primer combination are predicted to produce one or more amplicons having expected sizes in basepairs; (d) separating the amplicons by size, wherein the presence of: a 197 bp amplicon with the control primer combination is indicative of a CCR5 wildtype coding sequence; a 165 bp amplicon with the control primer combination is indicative of a CCR5-Δ32 coding sequence; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12 and a 309 bp amplicon with experimental primer combination SEQ ID Nos. 14 & 16 is indicative of a P*0101 CCR5 promoter allele; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13 and a 309 bp amplicon with experimental primer combination SEQ ID Nos. 14 & 16 is indicative of a P*0102 CCR5 promoter allele; a 363 bp amplicon with experimental primer combination SEQ ID Nos. 5 & 7, a 363 bp amplicon with experimental primer combination SEQ ID Nos. 5 & 9, a 367 bp amplicon with experimental primer combination SEQ ID Nos. 5 & 11, a 412 bp amplicon with experimental primer combination SEQ ID Nos. 5 & 13 and a 309 bp amplicon with experimental primer combination SEQ ID Nos. 14 & 16 is indicative of a P*0103 CCR5 promoter allele; a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a P*0201 CCR5 promoter allele; a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 15 & 16 is indicative of a P*0202 CCR5 promoter allele; (e) determining a CCR genotype for each sample based upon the CCR alleles indicated following step (d); and (f) compiling the genotypes determined in step (e), thereby genotyping the representative number of individuals in the population, thereby surveying CCR genotypes in the population.

The present invention is additionally directed towards a method of surveying HIV-1 co-receptor CCR alleles in an individual, comprising the steps of: (a) obtaining a biological sample from an individual, wherein the sample comprises genomic DNA; (b) combining a portion of the sample with at least one experimental primer combination and a control primer combination, thereby producing primer-annealed DNA, wherein the experimental primer combinations are selected from the group consisting of SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein the control primer combination is SEQ ID Nos. 17 & 18; (c) amplifying the primer-annealed DNA in a reaction, thereby producing amplicons, wherein reaction conditions for the amplification are optimized for sequence-specific amplification, wherein each experimental primer combination and the control primer combination are predicted to produce one or more amplicons having expected sizes in basepairs; and (d) separating the amplicons by size, wherein the presence of: a 197 bp amplicon with the control primer combination is indicative of a CCR5 wildtype coding sequence: a 165 bp amplicon with the control primer combination is indicative of a CCR5-Δ32 coding sequence; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12 and a 309 bp amplicon with experimental primer combination SEQ ID Nos. 14 & 16 is indicative of a P*0101 CCR5 promoter allele; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13 and a 309 bp amplicon with experimental primer combination SEQ ID Nos. 14 & 16 is indicative of a P*0102 CCR5 promoter allele; a 363 bp amplicon with experimental primer combination SEQ ID Nos. 5 & 7, a 363 bp amplicon with experimental primer combination SEQ ID Nos. 5 & 9, a 367 bp amplicon with experimental primer combination SEQ ID Nos. 5 & 11, a 412 bp amplicon with experimental primer combination SEQ ID Nos. 5 & 13 and a 309 bp amplicon with experimental primer combination SEQ ID Nos. 14 & 16 is indicative of a P*0103 CCR5 promoter allele; a 363 bp amplicon with experimental primer combination SEQ ID Nos. 6 & 8, a 412 bp amplicon with experimental primer combination SEQID Nos. 6 & 13 and a 309 bp amplicon with experimental primer combination SEQ ID Nos. 14 & 16 is indicative of a P*0201 CCR5 promoter allele; a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 15 & 16 is indicative of a P*0202 CCR5 promoter allele.

The present invention is further directed towards a method of predicting the disease progression to AIDS in an HIV-1-infected individual, comprising the steps of: (a) obtaining a biological sample from an individual, wherein the sample comprises genomic DNA; (b) combining a portion of the sample with at least one experimental primer combination and a control primer combination, thereby producing primer-annealed DNA, wherein the experimental primer combinations are selected from the group consisting of SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein the control primer combination is SEQ ID Nos. 17 & 18; (c) amplifying the primer-annealed DNA in a reaction, thereby producing amplicons, wherein reaction conditions for the amplification are optimized for sequence-specific amplification, wherein each experimental primer combination and the control primer combination are predicted to produce one or more amplicons having expected sizes in basepairs; (d) separating the amplicons by size, wherein the presence of: a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a CCR5 promoter genotype of P*0201/P*0201; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13, a 363 bp amplicon with experimental primer combination SEQ ID Nos. 6 & 8, a 412 bp amplicon with experimental primer combination SEQ ID Nos. 6 & 13, a 309 bp amplicon with experimental primer combination SEQ ID Nos. 14 & 16 and a 309 bp amplicon with experimental primer combination SEQ ID Nos. 15 & 16 is indicative of a CCR5 promoter genotype of P*0102/P*0202; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12, a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a CCR5 promoter genotype of P*0101/P*0201; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12, a 363 bp amplicon with experimental primer combination SEQ ID Nos. 6 & 8, a 412 bp amplicon with experimental primer combination SEQ ID Nos. 6 & 13, a 309 bp amplicon with experimental primer combination SEQ ID Nos. 14 & 16 and a 309 bp amplicon with experimental primer combination SEQ ID Nos. 15 & 16 is indicative of a CCR5 promoter genotype of P*0101/P*0202; wherein a CCR5 promoter genotype of P*0201/P*0201 or P*0102/P*0202 is predictive of an accelerated rate of AIDS progression in the individual (relative to an individual who does not possess the P*0201/P*0201 or P*0102/P*0202 gentoype), wherein a CCR5 promoter genotype of P*0101/P*0201 or P*0101/P*0202 is predictive of a slower rate of AIDS progression in the individual (relative to an individual who does not possess the P*0101/P*0201 or P*0101/P*0202 gentoype).

The present invention is also directed towards a method of predicting the probability of HIV-1 infection in an individual, comprising the steps of: (a) obtaining a biological sample from an individual, wherein the sample comprises genomic DNA; (b) combining a portion of the sample with at least one experimental primer combination and a control primer combination, thereby producing primer-annealed DNA, wherein the experimental primer combinations are selected from the group consisting of SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein the control primer combination is SEQ ID Nos. 17 & 18; (c) amplifying the primer-annealed DNA in a reaction, thereby producing amplicons, wherein reaction conditions for the amplification are optimized for sequence-specific amplification, wherein each experimental primer combination and the control primer combination are predicted to produce one or more amplicons having expected sizes in basepairs; and (d) separating the amplicons by size, wherein the presence of: a 363 bp with experimental primer combination SEQ ID Nos. 6 & 8, a 412 bp with experimental primer combination SEQ ID Nos. 6 & 13 and a 309 bp with experimental primer combination SEQ ID Nos. 14 & 16 is indicative of a CCR5 promoter genotype of P*0201/P*0201; a 363 bp with experimental primer combination SEQ ID Nos. 5 & 7, a 367 bp with experimental primer combination SEQ ID Nos. 5 & 10, a 412 bp with experimental primer combination SEQ ID Nos. 5 & 12 and a 309 bp with experimental primer combination SEQ ID Nos. 14 & 16 is indicative of a CCR5 promoter genotype of P*0101/P*0101; wherein a CCR5 promoter genotype of P*0201/P*0201 is predictive of a decreased probability of HIV-1 infection in the individual (relative to an individual who does not possess the P*0201/P*0201 genotype), wherein a CCR5 promoter genotype of P*0101/P*0101 is predictive of an increased probability of HIV-1 infection in the individual (relative to an individual who does not possess the P*0101/P*0101 genotype).

The present invention is yet further directed towards a method of correlating CCR genotypes with HIV-1 transmission and/or disease progression, comprising the steps of: (a) obtaining biological samples from a representative number of individuals, wherein each sample is from a different individual, wherein the sample comprises genomic DNA; (b) assessing each individual's HIV-1 status and/or risk of acquiring HIV-1; (c) assigning each individual to a risk group, wherein the assignment is based upon the individual's HIV-1 status and/or risk of acquiring HIV-1; (d) combining a portion of each sample with at least one experimental primer combination and a control primer combination, thereby producing primer-annealed DNA, wherein the experimental primer combinations are selected from the group consisting of SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein the control primer combination is SEQ ID Nos. 17 & 18; (e) amplifying the primer-annealed DNA in a reaction, thereby producing amplicons, wherein reaction conditions for the amplification are optimized for sequence-specific amplification, wherein each experimental primer combination and the control primer combination are predicted to produce one or more amplicons having expected sizes in basepairs; and (f) separating the amplicons by size, wherein the presence of: a 197 bp amplicon with the control primer combination is indicative of a CCR5 wildtype coding sequence; a 165 bp amplicon with the control primer combination is indicative of a CCR5-Δ32 coding sequence; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12 and a 309 bp amplicon with experimental primer combination SEQ ID Nos. 14 & 16 is indicative of a P*0101 CCR5 promoter allele; a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13 and a 309 bp amplicon with experimental primer combination SEQ ID Nos. 14 & 16 is indicative of a P*0102 CCR5 promoter allele; a 363 bp amplicon with experimental primer combination SEQ ID Nos. 5 & 7, a 363 bp amplicon with experimental primer combination SEQ ID Nos. 5 & 9, a 367 bp amplicon with experimental primer combination SEQ ID Nos. 5 & 11, a 412 bp amplicon with experimental primer combination SEQ ID Nos. 5 & 13 and a 309 bp amplicon with experimental primer combination SEQ ID Nos. 14 & 16 is indicative of a P*0103 CCR5 promoter allele; a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a P*0201 CCR5 promoter allele; a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 15 & 16 is indicative of a P*0202 CCR5 promoter allele; (g) determining a CCR genotype for each sample based upon the CCR alleles indicated following step (f); and (h) analyzing the genotypes determined in step (g), thereby genotyping the representative number of individuals with respect to the risk group assigned each individual, thereby correlating CCR genotypes with HIV-1 transmission and/or disease progression. Representative biological samples include blood, serum, saliva, semen, tissue biopsy and isolated DNA. Generally, separation is by gel electrophoresis, but may also be by means such as size fractionation. A preferred method of amplification includes polymerase chain reaction (PCR). Typical means of analysis include two-tailed Fisher's exact test, multiple logistic regression analysis, univariate analysis and multivariate analyses.

The present invention is additionally directed towards the oligonucleotides shown in SEQ ID Nos. 2–16.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (2nd Ed.)", (1989); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein, the normal convention of giving only the sequence in the 5' to 3' direction along the nontranscribed strand of DNA is used (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. Transcriptional and translational control sequences are DNA regulatory sequences, such as promoters, enhancers, polyadenylation signals, terminators, and the like, that provide for the expression of a coding sequence in a host cell. A "cDNA" is defined as copy-DNA or complementary-DNA, and is a product of a reverse transcription reaction from an mRNA transcript.

A "promoter sequence" is a DNA regulatory region capable of binding RNA polymerase in a cell and initiating transcription of a downstream (3' direction) coding sequence. Within the promoter sequence will be found a transcription initiation site, as well as protein binding domains (consensus sequences) responsible for the binding of RNA polymerase.

As used herein, the terms "restriction endonucleases" and "restriction enzymes" refer to enzymes which cut double-stranded DNA at or near a specific nucleotide sequence.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15–25 or more nucleotides to maintain specificity, although it may contain fewer nucleotides.

Primers are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the term "allele" is defined as the combination of polymorphic nucleotides at a given site on a chromosome.

As used herein, the term "genotype" is defined as the combination of two alleles in a given individual.

As used herein, the term "sequence-specific amplification" refers to PCR using sequence-specific primers that only produce amplicon(s) when the target sequence is present.

The following examples are given for the purpose of illustrating various embodiments of the invention and are not meant to limit the present invention in any fashion:

EXAMPLE 1

Human Subjects

Subjects from 2 established cohorts were studied; one in Kigali, Rwanda, and the other in New York City. Sociodemographic characteristics and epidemiological findings have been described elsewhere for these cohorts (20–23). The Kigali cohort (20,21) included 202 seropositive women with adequate follow-up since 1986. One of these subjects did not yield complete genotyping data and was excluded from further analysis. The cohort additionally included 77 seronegative women. Categorization of subjects were based on their clinical outcomes in combination with laboratory findings as defined by the Kigali staging system (21). Three subgroups of Kigali's were established: 15 rapid progressors (RPs) who died from AIDS in <6 years; 100 slow progressors (SPs) who remained asymptomatic for >10 years, and subjects that could not be classified definitively based on disease progression were treated as indeterminants (n=53) and combined with intermediate progressors (n=33) who had less extreme clinical outcome in the period of 6–10 years after seroconversion.

The clinical and epidemiologic categorization of the subset of heterosexual HIV-1-positive Rwandan women available for genetic studies have been summarized. For the 77 seronegative and the 201 seropositive women, the following risk factors were analyzed: 1) currently living alone but having multiple sexual partners or currently living with a single partner but both partners having extramarital affairs; 2) history of sexually transmitted disease in the past five years; 3) having multiple lifetime sexual partners; and 4) no condom use during sex in the last 2 years.

The Bronx, New York cohort consisted of subsets of injecting drug users recruited from three ethnic groups, including 58 Caucasians, 135 Hispanics, and 35 African-Americans (22,23). From the New York cohort of injecting drug users, 141 individuals were selected who remained seronegative despite high risk (based on a combination of the following non-exclusive risk behaviors) and 87 who became infected despite relatively little such risk or exposure: 1) having sex with another injecting drug user; 2) sharing needles in shooting galleries; 3) attending shooting galleries; and 4) sharing needles with strangers. Men having sex with other men was another risk factor observed in the overall New York cohort, but not in the subset of subjects studied here. Studies in both cohorts conformed to the procedures for informed consent approved by local and/or sponsoring institutional review boards.

EXAMPLE 2

Primate Species

Non-human primates, including 2 chimpanzees (*Pan troglodytes*), 2 pig-tailed macaques (*Macaca nemestrina*), and 2 sooty mangabeys (*Cercocebus atys*) were studied for their CCR5 promoter polymorphisms. Their CCR5 promoter sequences were amplified by PCR and analyzed by automated sequencing as for human samples.

EXAMPLE 3

Tenotyping Materials

DNA samples used throughout the study were extracted from whole buffy coats or precipitates of cervicovaginal fluids, using the standard salting out procedures (24,25) and QIAamp blood kit (QIAGEN Inc., Chatsworth, Calif., USA), respectively.

EXAMPLE 4

Genotyping Procedures

Genotyping of CCR5-Δ32 by PCR amplification size polymorphism and CCR2b-64I by PCR-RFLP was performed (1,4). Typing of CCR5 promoter variants was initially achieved through automated sequencing of PCR-amplified products. The CCR5-Δ32 and CCR2b-64I are approximately 2 kb downstream and 12.7 k b upstream, respectively, from the CCR5 downstream promoter that spans nucleotide 59052G (in the extended loci as defined by GenBank sequence U59626) to 59530C (13).

Typing of CCR5 promoter variants was initially achieved through automated sequencing of PCR-amplified products corresponding to nucleotide position 59012G to 59943G. Briefly, the design of allele-specific PCR amplification primers took advantage of the dimorphic site at nucleotide position 59029 (relative to Genbank accession number U95626), 20 bp upstream from the first nucleotide of the minimum CCR5 promoter segment (14). Two separate PCR reactions were performed for each sample: the first using the 59029G-specific forward primer (nucleotides 59012G→59029G) and common reverse primer (CCR5P-COM3N, 59925G←59943G), the second using the 59029A-specific forward primer (59012G→59029A) and primer CCR5P-COM3N.

PCR conditions were optimized to allow sequence-specific amplification determined by the 59029G/A-specific primers: each 12.5 $\mu$l PCR consisted of 1× buffer C (60 mM Tris-HCl (pH 8.5), 15 mM $(NH_4)_2SO_4$, 2.5 mM $MgCl_2$), 0.3 units of AmpliTaq polymerase, together with 0.5 $\mu$M of each primer, 80 ng genomic DNA, 0.2 mM each of dGTP, dCTP, dTTP and dATP. The PCR mix was subjected to 10 cycles of denaturing at 95° C. for 25 sec, annealing at 59° C. for 40 sec, and extension at 72° C. for 50 sec, followed by 23 cycles of denaturing at 95° C. for 25 sec, annealing at 55° C. for 40 sec, and extension at 72° C. for 50 sec. Samples yielding a 932-bp amplicon were diluted 1:40 in TEbuffer (10 mM Tris-HCl (pH 8.0), 2 mM EDTA) and 1.0 $\mu$l of the diluted product served as template for a 50-$\mu$l second-round PCR with a biotinylated reverse primer (CCR5P-COMR, 59709T←59729T) and a forward M13 (18 mer)-tailed primer (M13-CCR5P, 59012G→59028G).

After a further 22 cycles of denaturing at 95° C. for 25 sec, annealing at 59° C. for 40 sec, and extension at 72° C. for 50 sec, the resulting products were bound to streptavidin-coated combs and single-stranded templates were generated and sequenced using a Cy5-labelled universal M13 primer (5'-ACA GGA AAC AGC TAT GAC-3'; SEQ ID No. 1), a Cy5-labelled internal primer (CCR5PSBT, 59291T→59310A), and the ALFexpress autoload sequencing procedures (Pharmacia Biotech, Inc., Piscataway, N.J., USA). The allelic sequencing strategy outlined above resolved all known polymorphic sites in the constitutive downstream CCR5 promoter region without cloning and its attendant problems due to PCR-introduced nucleotide substitution (26). The reliability of data generated by automated sequencing was further confirmed by sequencing the complementary strand.

To expedite the genotyping procedures, 15 pairs of sequence-specific primers (SSP) were used to type the 5 major CCR5 promoter alleles simultaneously with the CCR5 and CCR2b variants (Tables 1 & 2). The final conditions for SSP-based typing were as follows: 1) Each 10 $\mu$l PCR solution contained 1× buffer C, 50–70 ng of genomic DNA, 0.3 units of AmpliTaq polymerase (Fisher Scientific, Norcross, Ga., USA), 120 nM of each control primer, 250 nM each of specific primer, 0.4 mM each of dGTP, dCTP, dTTP and dATP, 10% (v/v) glycerol, and 0.02% cresol red; 2) PCR cycle reactions were performed on an UNO-thermoblock (Biometra, Inc., Tampa, Fla., USA) for 10 higher-stringency cycles of denaturing at 94° C. for 25 sec, annealing at 60° C. for 45 sec, and extension at 72° C. for 45 sec, followed by 21 additional lower-stringency cycles of denaturing at 94° C. for 25 sec, annealing at 57° C. for 40 sec, and extension at 72° C. for 40 sec; 3) all PCR reactions were done in 96-well microtiter plates, each capable of typing 6 individual samples; 4) before each cycle reaction, PCR began with a denaturing step at 95° C. for 2.5 min; 5) all PCR reactions included a final extension step at 72° C. for 6 min; 6) half of each PCR reaction product was loaded directly onto a 1.7% agarose gel for electrophoresis. The SSP-banding patterns were recorded on photographs of ethidium bromide-stained gels.

The use of PCR-SSP was limited to the identification of known genetic variants; novel alleles that may exist in different populations could either give rise to novel reaction patterns or be misclassified by the scheme used herein. The 67 samples from Kigali and New York typed by both sequencing and PCR-SSP demonstrated 100% consistency between the 2 methods (Table 3). Thus, new alleles were not encountered even when the number of genotyped samples increased.

TABLE 1

Oligo primers used for typing major polymorphisms in CCR9b, CCR5, and the CCR5 downstream promoter region

| Oligo name | Specificity* | 5'→3' sequence (underline = polymorphic) | Annealing position | SEQ ID No. |
|---|---|---|---|---|
| CCR2b-5/1S | CCR2b-64V | tgggcaacatgctggtcg | 46278→46295 | 2 |
| CCR2b-5/2S | CCR2b-64I | tgggcaacatgctggtca | 46278→46295 61619→61636 | 3 |
| CCR2b-3/1G | general | tggaaaataagggccacagac | 46670←46690 | 4 |
| CCR5P-5/1S | 59029G | gagtggagaaaaggggg | 59012→59029 | 5 |
| CCR5P-5/2S | 59029A | gagtggagaaaagggga | 59012→59029 | 6 |
| CCRSP-3/1S | 59353T;59356C | agaatagatctctggtct-gaaa | 59353←59374 | 7 |
| CCR5P-3/2S | 59353C | agaatagatctctggtct-gaag | 59353←59374 | 8 |
| CCR5P-3/3S | 59353T;59356T | gagaatagatctctg-gtctaaaa | 59353←59375 | 9 |
| CCR5P-3/4S | 59356C | tagagaatagatctctg-gtctg | 59356←59377 | 10 |
| CCR5P-3/5S | 59356T | tagagaatagatctctg-gtcta | 59356←59377 | 11 |
| CCR5P-3/6S | 59402G | agaatcagagaacagttct-tcc | 59402←59423 | 12 |
| CCR5P-3/7S | 59402A | agaatcagagaacagttct-tct | 59402←59423 | 13 |
| CCR5P-5/3S | 59653C | caggaaacccatagaagac | 59635→59653 | 14 |
| CCR5P-5/4S | 59653T | caggaaacccatagaagat | 59635→59653 | 15 |
| CCR5P-3/8G | general | gtgggcacatattcagaag | 59925←59943 | 16 |
| CCR5-SP4G | general | tcattacacctgcagctctc | 62004→62023 | 17 |
| CCR5-PM6G | general | tggtgaagataagcctcac | 62182←62200 | 18 |

*The numbering of nucleotide positions is based upon GenBank sequence U95626.

TABLE 2

Primer mixes used in PCR-SSP-based typing of major polymorphisms in the CCR2b, CCR5 and the CCR5 promoter

| Primer mixes | Specificity[a] | Size of PCR amplicon |
|---|---|---|
| 1a = CCR2-5/1S + CCR2-3/1G | CCR2b-64Val | 413 bp |
| 1b = CCR2-5/2S + CCR2-3/1G | CCR2b-64Ile; CCR5 | 413; 585 bp |

TABLE 2-continued

Primer mixes used in PCR-SSP-based typing of major polymorphisms in the CCR2b, CCR5 and the CCR5 promoter

| Primer mixes | Specificity[a] | Size of PCR amplicon |
|---|---|---|
| 2a = CCR5P-5/1S + CCR5P-3/1S | 59029G–59353T | 363 bp |
| 2b = CCR5P-5/1S + CCR5P-3/2S | 59029G–59353C | 363 bp |
| 2c = CCR5P-5/2S + CCR5P-3/1S | 59029A–59353T | 363 bp |
| 2d = CCR5P-5/2S + CCR5P-3/2S | 59029A–59353C | 363 bp |
| 2e = CCR5P-5/1S + CCR5P-3/3S | 59029G–59353T–59356T | 364 bp |
| 3a = CCR5P-5/1S + CCR5P-3/6S | 59029G–59402G | 412 bp |
| 3b = CCR5P-5/1S + CCR5P-3/7S | 59029G–59402A | 412 bp |
| 3c = CCR5P-5/2S + CCR5P-3/6S | 59029A–59402G | 412 bp |
| 3d = CCR5P-5/2S + CCR5P-3/7S | 59029A–59402A | 412 bp |
| 4a = CCR5P-5/3S + CCR5P-3/8G | 59653C | 309 bp |
| 4b = CCR5P-5/4S + CCR5P-3/8G | 59653T | 309 bp |
| 5a = CCR5P-5/1S + CCR5P-3/4S | 59029G–59356C | 367 bp |
| 5b = CCR5P-5/1S + CCR5P-3/5S | 59029G–59356T | 367 bp |
| Control = CCR5-SP4G + CCR5-PM6G | CCR5 Δ32 WT | 165 bp 197 bp |

[a]The numbering of nucleotide positions is based upon GenBank sequence U95626.

TABLE 3

Extended CCR5 downstream promoter alleles obtained by allelic sequencing of PCR products derived from 67 selectively sequenced samples

| Allele designations | n | 59029 sequence | Combinations of polymorphic sites[b] | 59653 sequence | SEQ ID No. |
|---|---|---|---|---|---|
| CCR5P*0101 | 15 | G | $T_{59353}$-$C_{59356}$-$G_{59402}$-$G_{59648}$ (=P4) | C | 24 |
| CCR5P*0102 | 19 | G | $T_{59353}$-$C_{59356}$-$A_{59402}$-$G_{59648}$ (=P2) | C | 25 |
| CCR5P*0103 | 21 | G | $T_{59353}$-$T_{59356}$-$A_{59402}$-$G_{59648}$ (=P3) | C | 26 |
| CCR5P*0104 | 1 | G | $T_{59353}$-$C_{59356}$-$A_{59402}$-$A_{59648}$ (=P2) | C | 27 |
| CCR5P*0201 | 22 | A | $C_{59353}$-$C_{59356}$-$A_{59402}$-$G_{59648}$ (=P1) | C | 28 |
| CCR5P*0202 | 56 | A | $C_{59353}$-$C_{59356}$-$A_{59402}$-$G_{59648}$ (=P1) | T | 29 |

[a]Allelic sequences P*0101, P*0102, P*0103, P*0201 and P*0202 have been deposited in GenBank with Accession numbers AF109379, AF109380, AF109381, AF109382, AF109383, respectively. Allele P*0104 was only observed once.
[b]The numbering of nucleotide positions is based on GenBank sequence U95626. Polymorphism at position 59029 corresponds to the classification of an earlier study (5).
[c]This region has also been studied (6) and the alternative allele nomenclature is shown in parentheses.

EXAMPLE 5

Linkage Analysis of Genetic Variants at the CCR2h, CCR5, and CCR5 Promoter Loci

Linkage between allelic variants at different loci are typically estimated with data from families (27), which were not available in the cohorts studied herein. Instead, "apparent" 2-locus linkage was determined by $\chi^2$ tests for a 2x2 table containing the numbers of individuals with both, one without the other, or neither of the 2 markers in question (28). A p value documenting a significant association of two alleles (i.e., suggesting linkage disequilibrium) did not eliminate the possibility of their coincident occurrence on opposite chromosomes. Conversely, fully reliable two-locus haplotypes could be established only when alleles at one of the two loci were homozygous, and only such haplotypes were accepted for analysis.

EXAMPLE 6

Phylogenetic Analyses of CCR5 Promoter Sequences

The phylogenetic relationships among allelic sequences from human and non-human primates species were analyzed using software in the PHYLIP (29) and PAUP (30) packages. All CCR5 promoter sequences were aligned manually, with gaps introduced to increase alignment of sequences from primates. The final data set contained sequences spanning from nucleotide position 59029 (in the extended loci as defined by GenBank sequence U59626) to 59940.

EXAMPLE 7

Genotyping of CCR2b-64I by PCR-RFLP and PCR with Sequence-specific Primers(SSP)

The CCR2b-64 polymorphisms were determined by PCR-RFLPbased on an amplification-created restriction site in the 129-bp fragment (4) corresponding to nucleotide positions 46275 to 46403 (relative to U95626). The CCR2b-64I-bearing sequence could be digested by BsaBI into two fragments of 18 bp and 111 bp, while the sequence carrying the CCR2b-64V was refractory to digestion. To differentiate the CCR2b-64V from CCR2b-64I, PCR-SSP was used in two separate PCR reactions with both control and sequence-specific primer sets.

EXAMPLE 8

Genotyping of CCR5-Δ32 hy PCR Amplification Size Polymorphism

PCR amplification of the CCR5 coding sequences corresponding to nucleotide positions 62004–62183 (relative to U95626) differentiated the CCR5-Δ32 and wild type alleles (1), producing a 180-bp amplicon for the wild type sequence and a 148-bp product for the deletion sequence. Additional primers were also used to amplify the deletion region for sequencing and size differentiation in a PCR-SSP format.

EXAMPLE 9

Simultaneous Genotyping of CCR2b, CCR5, and CCR5 Promoter Polymorphisms Based on PCR-SSP To facilitate simultaneous PCR-SSP-based typing of the dimorphisms CCR2b-64V/I, CCR5 wild type/CCR5-Δ32, and CCR5 promoter alleles P*0101, P*0102, P*0103, P*0201 and P*0202, a panel of 21 individual primers were selected based upon a) similar melting temperatures; b) no mispriming; c) no strong secondary structure; d) no homodimer/heterodimer formation. The first 12 primer mixes were adequate for the routine genotyping of each sample. Three additional primer mixes were required to confirm samples carrying CCR5P*0103, which gave weak positive signals in reaction 2a due to the presence of 59356T. Samples whose CCR5 promoter variants were genotyped by sequencing and whose CCR2b dimorphism was genotyped by PCR-RFLP (4) served as reference materials for testing the reliability of the PCR-SSP assay. Different thermostable DNA polymerases including AmpliTaq (Promega, Madison, Wis., USA) and Platinum Taq (Life Technologies, Gaithersburg, Md., USA) yielded comparable data sets, showing 100% consistency between PCR-SSP and sequencing and between PCR-SSP and RFLP.

Using the PCR-SSP format, the CCR5 genotype could be assigned according to the size of the SSP control product amplified by primers flanking the 32-bp deleted region. Confirmatory product was also available in SSP reaction 1b: primer CCR2b-5/2S (also CCR2b-64I-specific) and primer CCR5-PM6G (CCR5-general) in this multiplex reaction amplify a larger fragment spanning the 32-bp deletion region in CCRS. As a result, the undeleted wild type CCR5 sequence gave rise to a 197 bp product in all 12 reactions as well as a 585 bp product in reaction 1b, while the CCR5-Δ32 genotype produced 165 bp and 553 bp amplicons in the corresponding reactions. The CCR5-specific product from reaction 1b was also tested by RFLP for the presence of the CCR5-m303 polymorphism (45), which were uncommon or absent in other populations (1,43,48) as well as in the New York and Rwandan subjects tested here.

EXAMPLE 10

Statistical Analysis

Kigali and New York subjects were analyzed separately; New York subjects belonged to three ethnic groups and, as such, were analyzed separately and jointly. Standard procedures in EpiInfo software (33) were used to calculate $\chi^2$ and odds ratio calculations with 95% confidence intervals using differential distribution of genetic factors in subjects with varying rates of HIV-1 disease progression, to measure apparent linkage disequilibrium among CCR variants, and to evaluate associations of genetic and non-genetic risk factors with HIV-1 infection. Multiple logistic regression analysis by SAS (SAS Institute, Inc., Cary, N.C.) was performed by incorporating 1 ) all CCR and SDF1 variants; 2) ethnicity and age of participants; and 3 ) individual risk factors with significant associations with HIV-1 infection (Kigali) or individual risk factors used for selecting participants (New York). Multivariate analyses were also performed using a summary risk score, but this reduced model was less informative. Yates' corrected method or a two-tailed Fisher's exact test was applied to analyses with small numbers of observations.

EXAMPLE 11

Identification and Freqency of CCR5 Promoter Alleles and Other Related Markers Analyses yielded 6 different alleles and 15 genotypes in the cohort of Rwandan women, 9 of which were seen at a frequency higher than 5% (Table 4). Direct allele-level sequencing of the CCR5 promoter region spanning nucleotide 59029 to 59653 of PCR-amplified human genomic DNA revealed 6 CCR5 promoter alleles: five were common and one was observed in only a single individual (Table 3). The 5 common alleles (not including the rare polymorphism at position 59648) could theoretically produce 15 genotypes (allele combinations), 14 of which were observed in the 60+ samples examined herein. The 5 major allelic variants were defined by dimorphic sites at nucleotide positions 59029, 59353, 59356, 59402, and 59653 relative to GenBank sequence U59626. By this definition, allele sequences P*0101 and P*0201 matched GenBank sequences U95626 and AF031237, respectively.

Figure 3:
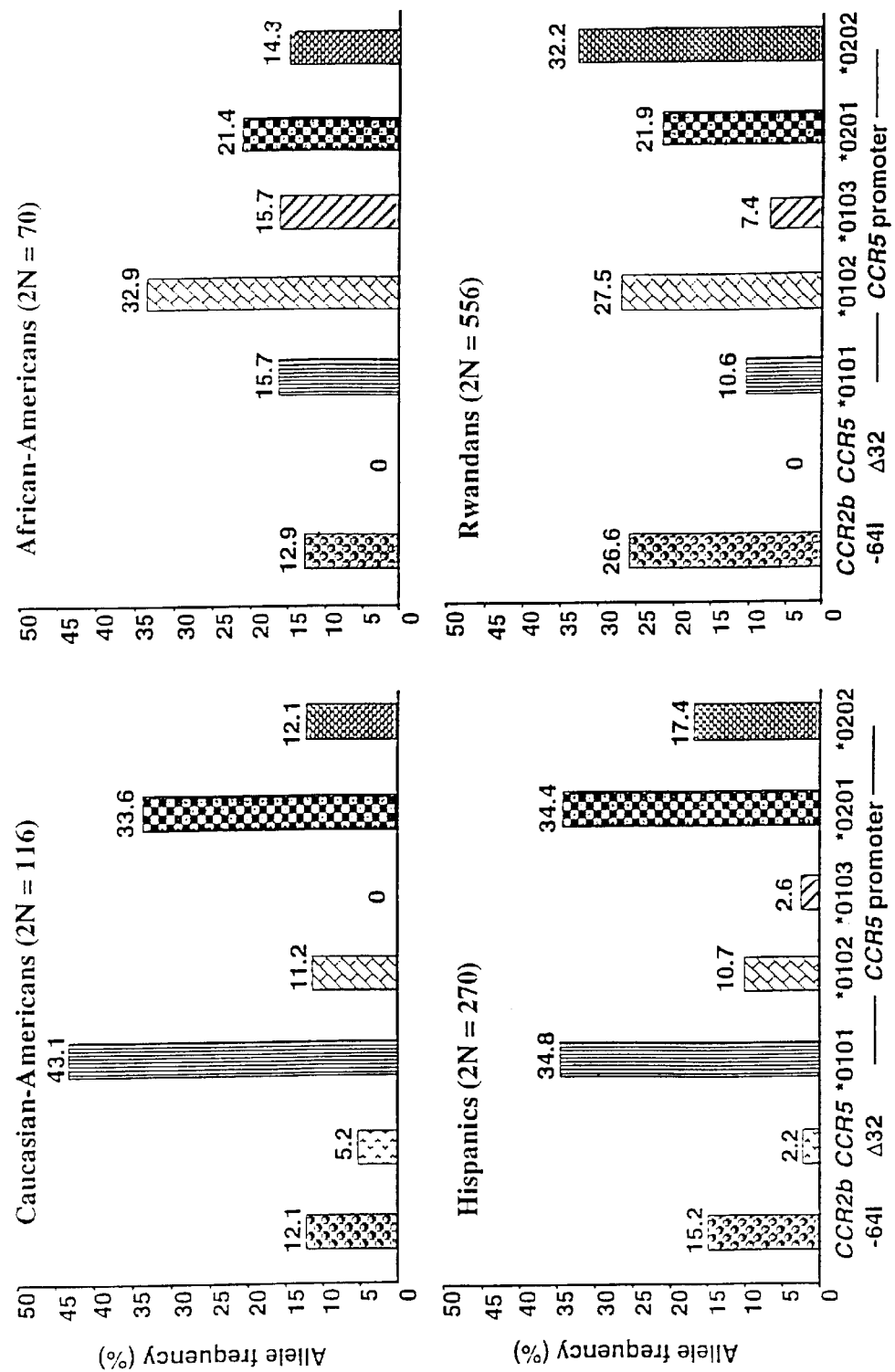
FIG. 3 shows the allelic frequencies of CCR2b-64I, CCR5-Δ32, and CCR5 promoter variants in four ethnic groups from the Bronx, N.Y. (Caucasians, African-Americans, and Hispanics) and Kigali, Rwanda. The CCR2b-64I is invariably linked to CCR5 promoter allele P*0202 in all 4 groups, while the Caucasian- and Hispanic-specific CCR5-Δ32 is exclusively linked to CCR5 promoter allele P*0201 (see Tables 5 & 6). The frequency of CCR5-Δ32 in Caucaisan-Americans studied herein was lower than those reported elsewhere.
Figure 4:
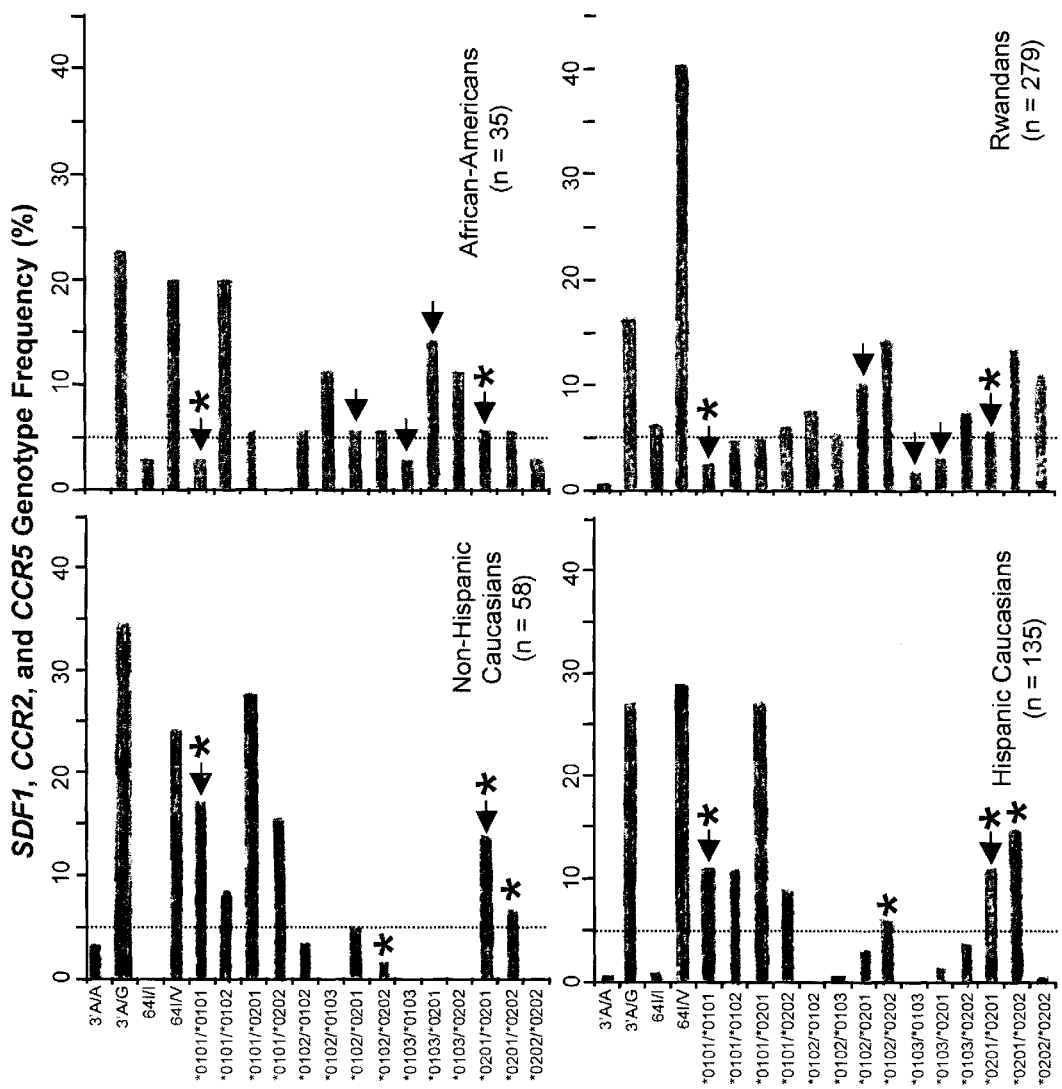
FIG. 4 shows the distribution of SDF1 and CCR genotypes in participants from Kigali, Rwanda and the Bronx, N.Y. Genotypes that appeared to mediate HIV-1 transmission in ethnic Africans (African-Americans and Rwandans) are indicated by arrows. Genotypes that appeared to mediate HIV-1 transmission in ethnic Caucasians (Caucasian-Americans and Hispanics) are indicated by asterisks. Genotypes showing associations with HIV-1 transmission in all ethnic groups are indicated by an arrow and an asterisk.

The distributions of CCR2b, CCR5, and CCR5 promoter variants differed widely among distinct ethnic groups (FIG. 3). Overall, 6 major ('major' is defined herein as having a frequency higher than 5%) CCR5 promoter genotypes were detected in Hispanics, 7 in Caucasian-Americans, 9 in African-Americans, and 10 in Rwandans (FIG. 4). Several genotypes were apparently restricted to certain ethnic groups, but the small number of subjects in the African-American and Caucasian-American groups did not allow reliable comparisons among populations surveyed here. Hispanic and non-Hispanic Caucasians resemble each other rather closely, and black African-Americans in New York and Rwandans also resemble each other in the distributions of promoter genotypic frequencies (FIG. 4). In particular, allele P*0103 was largely restricted to populations of African origin. As a result, there were more CCR5 promoter genotypes (allele combinations) in Africans than Caucasians and Hispanics. Multiple linkages among CCR2b, CCR5, and CCR5 promoter variants were consistent in all populations (Tables 5 & 6). For example, exclusive linkage of promoter allele P*0202 (59653T) to CCR2b-64I was consistent with an earlier observation in Caucasians (2). Meanwhile, promoter allele P*0201 was the only variant that was linked to CCRS-Δ32. Mutually exclusive linkages with P*0201 and P*0202 implied that CCR2b-64I and CCR5-Δ32 could not exist on the same chromosome, and the negative linkage between CCR2b-64I and CCR5-Δ32, as revealed by the analysis herein, confirmed this association (or lack, thereof) (Table 5).

Figure 5C:
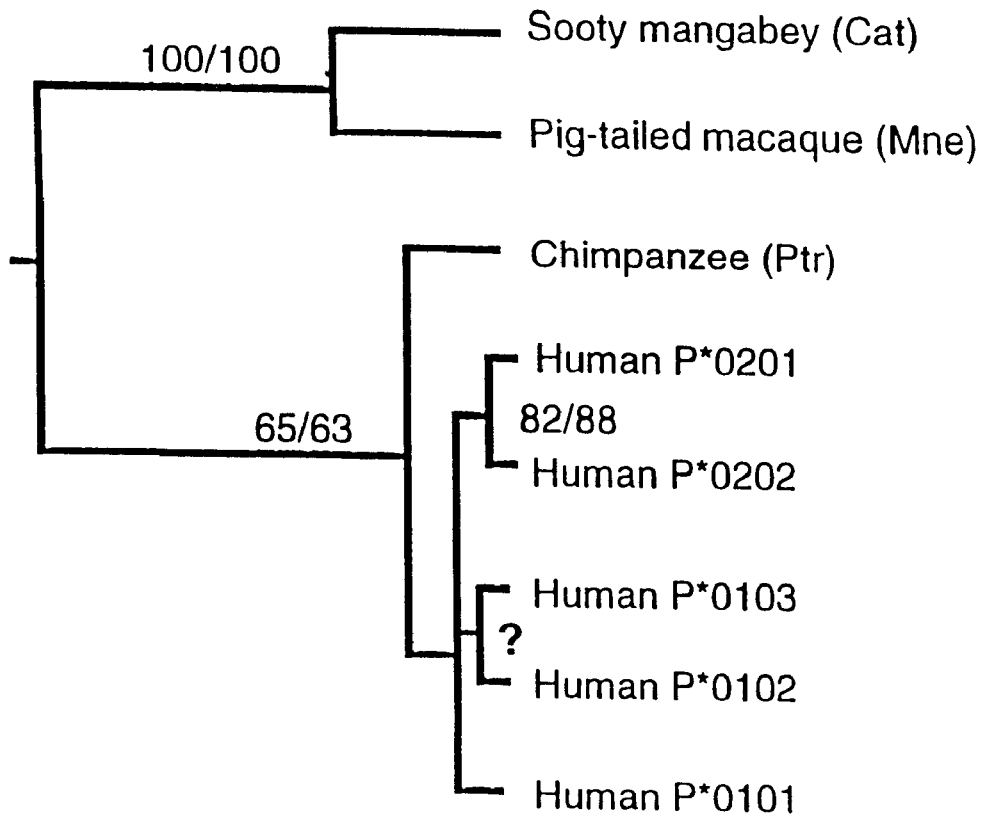
FIG. 5C shows phenogram based on maximum likelihood method. Numbers next to branches indicate the frequencies supported by bootstrap re-analyses of the sequence data using both neighbor-joining method (32) in the PHYLIP package (29) and parsimony method in the PAUP package (30). Grouping of human promoter allele P*0102 with P*0103 is not supported by neighbor-joining or parsimony analysis.

Sequences from non-human primates revealed differences in 2 of 6 putative transcription factor binding elements within the CCR5 promoter (FIG. 5A). As would be predicted, pair-wise genetic distance (FIG. 5B) and phylogenetic analyses (FIG. 5C) placed the chimpanzee CCR5 promoter sequence closer to all human CCRS promoter alleles than to alleles from other primate species. The ancestral lineage of human CCR5 promoter alleles appeared to be P*0102, which shared identical sequences with other non-human alleles at nucleotide positions that define all major promoter alleles in humans (i.e., 59029, 59353, 59356, 59402, and 59653). Moreover, P*0201 and P*0202 apparently diverged from the common ancestral sequence more recently than did other alleles. By the same analyses, polymorphisms at two positions, the G at 59029 and the T at 59353, appeared ancestral to any other lineages.

Finally, in all human and non-human alleles, exclusive linkage between the G-to-A nucleotide substitution at position 59029 to the T-to-C change at position 59356 presumably indicates either gene conversion or simultaneous point mutations. If the former is true, other upstream (CCR2b coding region) or downstream (CCR5 coding region) polymorphisms are likely to be linked in the same fashion. The CCR2b-64I-59653T linkage served as one example, and CCR5-Δ32-P*0201 linkage served as another. Thus, a disease association with an individual polymorphic site can actually signal relationships with one or more additional polymorphisms at multiple inter-linked positions.

TABLE 4

CCR2b and CCR5 promoter genotypes observed in HIV-1-infected Rwandan women

| Promoter genotypes | Expected frequency (%) | Observed frequency (%) |
|---|---|---|
| P*0101/*0101 | 1.2 | 3.0 |
| P*0101/*0102 | 7.9 | 6.0 |
| P*0101/*0103 | 1.8 | 0.0 |
| P*0101/*0201 | 4.2 | 4.5 |
| P*0101/*0202 | 7.9 | 6.0 |
| P*0102/*0102 | 6.8 | 12.4 |
| P*0102/*0103 | 4.3 | 0 |
| P*0102/*0201 | 4.9 | 6.0 |
| P*0102/*0202 | 18.4 | 15.4 |
| P*0103/*0103 | 0.7 | 2.5 |
| P*0103/*0201 | 3.1 | 2.5 |
| P*0103/*0202 | 5.8 | 9.0 |
| P*0104/*0202 | 0.2 | 0.5 |
| P*0201/*0201 | 3.6 | 5.5 |
| P*0201/*0202 | 13.3 | 13.9 |
| P*0202/*0202 | 12.5 | 12.9 |

TABLE 4-continued

CCR2b and CCR5 promoter genotypes observed in HIV-1-infected Rwandan women

| Promoter genotypes | Expected frequency (%) | Observed frequency (%) |
|---|---|---|
| CCR2b genotypes | | |
| 64V/I | 40.8 | 42.3 |
| 64I/I | 8.2 | 7.5 |

TABLE 5

Linkage among CCR2b, CCR5, and CCR5 promoter variants in subjects from the Bronx, New York[a]

| Variant 1 | Variant 2 | N[b] | 1+/2+ | 1+/2− | 1−/2+ | 1−/2− | OR | 95% CI | p |
|---|---|---|---|---|---|---|---|---|---|
| CCR2b-64I | CCR5-Δ32 | 193 | 1 | 53 | 11 | 128 | 0.22 | 0.03–1.74 | 0.118 |
| CCR2b-64I | CCR5 promoter | | | | | | | | |
| | P*0101 | 228 | 20 | 42 | 109 | 57 | 0.25 | 0.13–0.46 | 0.001 |
| | P*0102 | 228 | 10 | 52 | 46 | 120 | 0.50 | 0.24–1.07 | 0.071 |
| | P*0201 | 228 | 23 | 39 | 99 | 67 | 0.40 | 0.22–0.73 | 0.002 |
| | P*0202[c] | 228 | 62 | 0 | 7 | 159 | 23.7 | 11.5–49.0 | 0.001 |
| | 59029G[d] | 228 | 37 | 138 | 138 | 28 | 0.3 | 0.16–0.58 | 0.001 |
| CCR5-Δ32 | P*0201 | 193 | 12 | 0 | 97 | 84 | 1.87 | 1.63–2.14 | 0.002 |

[a]Subjects from Bronx included Caucasians (n = 58), Hispanics (n = 135), and African-Americans (n = 35).
[b]African-Americans (n = 35) are not included in the analysis involving CCR5-Δ32, as this variant is not present in this ethnic group.
[c]Promoter allele P*0202 exclusively carries 59653T (Table 3).
[d]50029G is exclusively linked to 59353T, and both occur at equal frequency in this cohort regardless of the ethnic group.

TABLE 6

Linkage analysis of CCR2b-64I and individual CCR5 promoter alleles and polymorphic sites in a cohort of 278 Rwandan women[a]

| Variant 1 | Variant 2 | N[b] | 1+/2+ | 1+/2− | 1−/2+ | 1−/2− | OR | 95% CI | p |
|---|---|---|---|---|---|---|---|---|---|
| CCR2b-64I | Promoter variants | | | | | | | | |
| | P*0101 | 15 | 115 | 38 | 110 | | 0.4 | 0.20–0.73 | 0.003 |
| | P*0102 | 33 | 97 | 87 | 61 | | 0.2 | 0.14–0.40 | 0.001 |
| | P*0201 | 33 | 97 | 73 | 75 | | 0.4 | 0.21–0.58 | 0.001 |
| | P*0202 | 129 | 1 | 19 | 129 | | 875.8 | 115.5–6639.7 | 0.001 |
| | 59029G[b] | 67 | 63 | 126 | 22 | | 0.2 | 0.10–0.33 | 0.001 |

[a]CR5-Δ32 is absent in this cohort.
[b]50029G is exclusively linked to 59353T, and both occur at equal frequency in this cohort.

EXAMPLE 12

CCR5 Promoter Genotypes and HIV-1 Infection

Seropositive and seronegative individuals consistently differed in their distributions of two CCR5 promoter genotypes: the homozygous genotype P*0101/*0101 was more frequent in seropositives than in seronegatives (Table 7), while homozygous or heterozygous genotypes involving allele P*0201 were more frequent in seronegatives than in seropositives (Table 7). Despite the tight linkages that existed among alleles of CCR2b, the CCR5 coding region, and the CCR5 promoter, the relationships between CCR5 promoter alleles and occurrence of HIV-1 infection could not be attributed to either CCR2b or variants in the CCR5 coding region (Table 8). Homozygosity and heterozygosity for SDF1-3′A, a polymorphism in the natural ligand of CXCR4 (54), were further excluded as a contributing factor.

Several CCR5 promoter genotypes demonstrated trend for association in either combined groups, probably as a result of ethnically specific effects. For example, the homozygous promoter form P*0103/*0103 was found in 6 (or 2.8%) HIV-1-infected black individuals but was absent from seronegatives (OR=5.8, p=0.097). This relationship was as strong as that recognized earlier for the P*0101/*0101 genotype.

The promoter allele P*0103 was largely restricted to blacks. Thus, the protective genotypes involving P*0201 could be split into 5 major genotypes (P*0101/*0201, P*0102/*0201, P*0103/*0201, P*0201/*0201, and P*0201/*0202) in black populations, but genotype P*0101/*0103 was not detected. In the Caucasoid group, P*0201 can form 4 genotypes, and one of these (P*0102/*0201) was rare. The re-analyses revealed that only genotypes P*0201/*0201 and P*0201/*0202 were associated with protection against infection in Cauicasoids (OR=0.5, p=0.032), compared with P*0102/*0201, P*0103/*0201, and P*0201/*0201 in blacks (OR=0.3, p=0.001). Another P*0201+ genotype P*0101/*0201 was equally distributed in seropositive and seronegative groups regardless of their ethnicity. Therefore, the relative contribution to protection by different genotypes involving allele P*0201 varied according to the ethnic background.

The relationships observed on CCR5 promoter genotypes remained the same when two additional non-CCR factors known to influence the rates of HIV-1 disease progression in this cohort were considered. Specifically, homozygosity at HLA class I A or B or both was strongly associated with more rapid disease progression in these Rwandan women, while HLA B*57 was associated with slower disease progression. Data from combinations of promoter and HLA factors strongly suggest that the protective effects of promoter genotypes P*0101/*0201 and P*0101/*0202 are independent of the HLA factors, as were the risk effects of P*0201/*0201 and P*0102/*0201 (Table 10).

The characterization of CCR5 promoter allelic sequences provided simple explanations for previous associations with disease progression (FIG. 6) and allowed further predictions. First, alleles P*0201 and P*0202 were the only promoter variants carrying the previously recognized disease-accelerating P1/P1 genotype (6). These two alleles carried exclusively 59029A and not the disease-delaying 59029G/G (5). As a result, P1/P1 homozygotes and 59029G/G-carriers represented 2 mutually exclusive groups of promoter genotypes. The association of the P1/P1-carrying P*0201/*0201 with more rapid disease progression as revealed by our data supported and refined the known effects of P1/P.

Figures 6A, 6B:
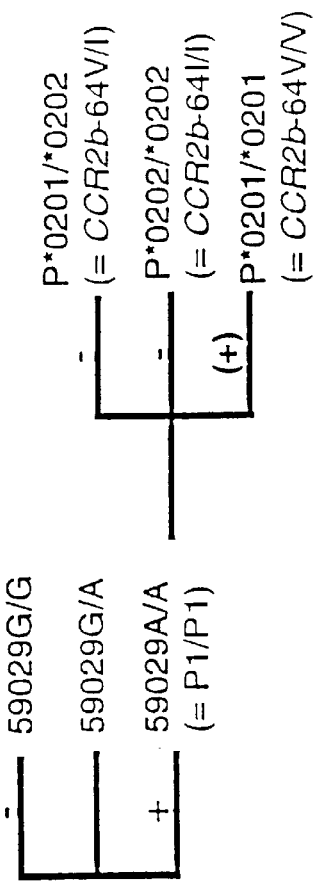
FIG. 6A shows the 5 major CCR5 promoter alleles (deposited in GenBank with accession numbers AF109379, AF109380, AF109381, AF109382, AF109383, respectively) found in various human ethnic groups are defined by 5 polymorphic sites in the region spanning nucleotide positions 59029 to 59653 (relative to GenBank accession number U59626).
FIG. 6B shows relationship between previously recognized CCR2b, CCR5 promoter genotypes and the CCR5 promoter alleles specified in (4A). The + and − indicate rapid and slow HIV-1 disease progression, respectively, as reported in several studies (4–6). The predicted effect (+, rapid progression) of the P*0201/*0201 genotype can be inferred from the reported studies.

Second, as noted above, P*0202 (59653T) is exclusively linked to CCR2b-64I (Tables 5 & 6), which has been associated with slower disease progression in cohorts of seroconverters (2,4,11,12). Thus, the relationship between P1/P1 genotype and rapid HIV-1 disease progression must depend upon P*0201 and not the CCR2b-64I-linked P*0202 (FIG. 6B). The lack of association between CCR2b-64I and slower disease progression in Rwandan women was seemingly inconsistent with findings from another African cohort (34). However, exclusive linkage of 59653T to CCR2b-64I (2), which in turn solely defines promoter allele P*0202, made these findings easily explainable. In other earlier studies, CCR2b-64I variant has been less clearly associated with slower disease progression in certain seroprevalent groups than in cohorts of seroconverters (2,4,10–12), perhaps as much because of their genetic heterogeneity as because of misclassification with respect to outcome. The contrasting relationships seen here with the CCR2b-64I-carrying P*0101/*0202 (protective) and P*0201/*0202 (risk) indicated clearly that the CCR2b-64I effect can go either way dependending upon the promoter genotypes. As a result, the CCR2b-64I effect must be secondary to polymorphisms in the promoter, which can vary significantly among different ethnic groups. The association between the P1/P1 variant and an accelerated course independent of CCR2b-64I (6), coupled with the preliminary demonstration of reduced promoter activity (5) in carriers of the 59029G variant that includes P*0101 and P*0102, enhances the likelihood that the effects of promoter polymorphisms are independent of CCR2b-64I.

TABLE 7

Distribution of CCR5 promoter genotypes in ethnic Africans and ethnic Caucasians

| Promoter Genotypes | HIV+ Blacks[a] (n = 213) | HIV− Blacks (n = 100) | OR (p) | Caucasoids HIV+ (n = 75) | Caucasoids HIV− (n = 118) | OR (p) |
|---|---|---|---|---|---|---|
| P*0101/*0101 | 3.3 (7)[b] | 0 | 6.8 (0.065) | 21.3 (16) | 7.6 (9) | 3.1 (0.010) |
| P*0101/*0102 | 6.6 (14) | 9.0 (9) | — | 12.0 (9) | 9.3 (11) | — |
| P*0101/*0201 | 4.7 (10) | 6.0 (6) | — | 25.3 (19) | 28.8 (34) | — |
| P*0101/*0202 | 5.6 (12) | 5.0 (5) | — | 8.0 (6) | 12.7 (15) | — |
| P*0102/*0102 | 12.2 (26) | 10.0 (10) | — | 0 | 1.7 (2) | — |
| P*0102/*0103 | 0.5 (1) | 4.0 (4) | 0.1 (0.038) | 1.3 (1) | 0 | — |
| P*0102/*0201 | 5.6 (12) | 19.0 (19) | 0.3 (0.001) | 4.0 (3) | 3.4 (4) | — |
| P*0102/*0202 | 15.0 (32) | 10.0 (10) | — | 8.0 (6) | 2.5 (3) | 3.3 (0.082) |
| P*0103/*0103 | 2.8 (6) | 0 | 5.8 (0.097) | 0 | 0 | — |
| P*0103/*0201 | 2.8 (6) | 8.0 (8) | 0.3 (0.042) | 2.7 (2) | 0 | — |
| P*0103/*0202 | 9.9 (21) | 4.0 (4) | 2.6 (0.054) | 1.3 (1) | 3.4 (4) | — |
| P*0201/*0201 | 5.2 (11) | 7.0 (7) | — | 6.7 (5) | 15.3 (18) | 0.4 (0.073) |
| P*0201/*0202 | 13.1 (28) | 12.0 (12) | — | 9.3 (7) | 14.4 (17) | — |
| P*0202/*0202 | 12.2 (26) | 6.0 (6) | 2.2 (0.092) | 0 | 0.8 (1) | — |

[a]One of the infected individual in this group carried the rare genotype P*0104/*0202.
[b]Numbers are expressed as % (n).

TABLE 8

Distribution of previously recognized factors in CCR5 promoter and CCR2b among seropositive and seronegative groups in Kigali, Rwanda and the Bronx, New York (NY)

| CCR variants | | Kigali-Rwandans | | NY-Caucasians | | NY-African Americans | | NY-Hispanics | | NY-combined | |
|---|---|---|---|---|---|---|---|---|---|---|---|
| | | + | − | + | − | + | − | + | − | + | − |
| | N= | 201 | 77 | 17 | 41 | 12 | 23 | 58 | 77 | 87 | 141 |
| 59029G/G[a] | % (n) | 23.9 (48) | 18.2 (14) | 24.4 (10) | 41.2 (7) | 39.1 (9) | 50 (6) | 15.6 (12) | 32.8 (19) | 22.0 (31) | 36.8 (32) |
| | OR (CI) | 1.4 (0.7–2.7) | | 0.5 (0.1–1.5) | | 0.6 (0.2–2.6) | | 0.4 (0.2–0.9) | | 0.5 (0.3–0.9) | |
| | p | 0.308 | | 0.205 | | 0.543 | | 0.019 | | 0.015 | |

TABLE 8-continued

Distribution of previously recognized factors in CCR5 promoter and CCR2b among seropositive and seronegative groups in Kigali, Rwanda and the Bronx, New York (NY)

| CCR variants | N= | Kigali-Rwandans + 201 | − 77 | NY-Caucasians + 17 | − 41 | NY-African Americans + 12 | − 23 | NY-Hispanics + 58 | − 77 | NY-combined + 87 | − 141 |
|---|---|---|---|---|---|---|---|---|---|---|---|
| +P1/+P1[a] | % (n) | 32.3 (65) | 26.0 (20) | 11.8 (2) | 24.4 (10) | 0 | 21.7 (5) | 17.2 (10) | (33.8 (26) | 13.8 (12) | 29.1 (41) |
|  | OR (CI) | 1.4 (0.7–2.7) |  | 0.4 (0.1–2.1) |  | 0.2[b] (0.0–3.0)[b] |  | 0.4 (0.2–0.9) |  | 0.4 (0.2–0.8) |  |
|  | p | 0.304 |  | 0.240 |  | 0.104 |  | 0.032 |  | 0.008 |  |
| CCR2b-64I[c] | % (n) | 49.8 (100) | 39.0 (30) | 11.8 (2) | 29.3 (2) | 33.3 (4) | 17.4 (4) | 29.3 (17) | 29.9 (23) | 26.4 (23) | 27.7 (39) |
|  | OR (CI) | 1.6 (0.9–2.6) |  | 0.3 (0.1–1.6) |  | 2.4 (0.5–11.9) |  | 1.0 (0.5–2.0) |  | 0.9 (0.5–1.7) |  |
|  | p | 0.107 |  | 0.139 |  | 0.257 |  | 0.944 |  | 0.841 |  |

[a] +P1/+P1 = 59029A/A = P*0201/*0201 + P*0201/*0202 + P*0202/*0202, which is mutually exclusive from 59029G/G = all genotypes involving only P*0101, P*0102, P*0103, and P*0104.
[b] An arbitrary value of 0.5 was used to replace 0 before calculation of odds ratio and CI.
[c] CCR2b-64I is exclusively linked to CCR5 promoter allele P*0202.

TABLE 9

Differential distribution of CCR5 promoter genotypes in HIV-1+ Rwandan women with varying rates of disease progression and a comparison with previously recognized promoter variants and the closely related CCR2b genotypes

| Observed genotypes | RPs[a] (N = 15) | IPs[a] (N = 86) | SPs[a] (N = 100) | p for trend |
|---|---|---|---|---|
| CCR5 promoter genotypes[b] defined here |  |  |  |  |
| 1. P*0101/*0201 | 0 | 2.3 (2)[c] | 6.9 (7) | 0.083 |
| 2. P*0101/*0202 | 0 | 1.2 (1) | 10.9 (11) | 0.005 |
| 1 + 2 | 0 | 3.5 (3) | 17.8 (18) | 0.001 |
| 3. P*0101/*0102[d] | 13.3 (2) | 5.8 (5) | 5.0 (5) | 0.318 |
| 4. P*0101/*0103[d]: not found | — | — | — | — |
| 5. P*0101/*0101[d] | 6.7 (1) | 1.2 (1) | 4.0 (4) | — |
| 3 + 4 + 5 = 3 + 5[d] | 20.0 (3) | 7.0 (6) | 9.0 (9) | — |
| 1 + 2 + 3 + 4 + 4 + 5 = 1 + 2 + 3 + 5[d] | 20.0 (3) | 10.5 (9) | 27.0 (27) | 0.030 |
| 6. P*0102/*0202 | 26.7 (4) | 18.6 (16) | 11.0 (11) | 0.058 |
| 7. P*0201/*0201 | 13.3 (2) | 7.0 (6) | 3.0 (3) | 0.072 |
| 6 + 7 | 40.0 (6) | 25.6 (22) | 14.0 (14) | 0.007 |
| 8. P*0202/*0202 | 6.7 (1) | 14.0 (12) | 13.0 (13) | — |
| Promoter genotypes recognized previously |  |  |  |  |
| 59029G/G[e] | 26.7 (4) | 20.9 (18) | 26.0 (26) | — |
| 59029A/A[e] = P1/P1[f] | 33.3 (5) | 34.9 (30) | 30.0 (30) | — |
| 59029G/A | 40.0 (6) | 44.2 (38) | 43.6 (44) | — |
| CCR2b genotypes |  |  |  |  |
| CCR2b-64I/V + 64I/I | 53.3 (8) | 50.0 (43) | 49.0 (49) | — |
| CCR2b-64I/V | 46.6 (7) | 43.0 (37) | 41.0 (41) | — |
| CCR2b-64I/64I | 6.7 (1) | 7.0 (6) | 8.0 (8) | — |

[a] The three groups of patients (see text) were classified according to their rates of disease progression: RPs = rapid progressors = deaths from AIDS in <6 years; SPs = slow progressors = no clinical manifestation of HIV-1-related diseases in >10 years; IPs = intermediate and indeterminant progressors with less extreme clinical outcomes.
[b] Fifteen major CCR5 promoter genotypes involving 5 major alleles were defined in this cohort. Only those involving alleles that appeared to distribute disproportionally (p ≦ 0.1) are shown.
[c] Numbers are expressed as % (n).
[d] All genotypes carry homozygous 59029G/G.
[e] 59029G/G (5) are represented by 6 major genotypes in this cohort: P*0101/*0101, P*0101/*0102, P*0101/*0103, P*0102/*0102, P*0102/*0103, P*0103/*0103; none of them appeared to have biased distribution among the three groups of subjects.
[f] The P1 genotype (6) consists of 2 distinct alleles (*0201 and *0202) in this cohort as defined by the polymorphism at nucleotide position 59653 (GenBank U59626).

TABLE 10

Analyses of combinations of disease-related factors specifically recognized in HIV-1 seropositive Rwandan women

| Promoter genotypes | Presence or absence of other recognized factors | RPs % (n) | IPs % (n) | SPs % (n) | p for trend |
|---|---|---|---|---|---|
| 1 + 2[a] | +Hmz[b] at A, B, or both | 0 | 0 | 2.0 (2) | 0.193 |
|  | +Htr[b] at A, B, or both | 0 | 3.5 (3) | 16.0 (16) | 0.002 |
|  | +B*57 | 0 | 0 | 3.0 (3) | 0.109 |
|  | −B*57 | 0 | 3.5 (3) | 15.0 (15) | 0.009 |
|  | −Hmz[a] − B*57 | 0 | 3.5 (3) | 13.0 (13) | 0.010 |
| P*0201/*0201 | +Hmz[b] at A, B, or both | 6.7 (1) | 1.2 (1) | 0 | 0.037 |
|  | +Htr[b] at A, B, or both | 6.7 (1) | 5.8 (5) | 3.0 (3) | 0.327 |
|  | +B*57 | 0 | 1.2 (1) | 0 | 0.500 |
|  | −B*57 | 13.3 (2) | 5.8 (5) | 3.0 (3) | 0.096 |
|  | −Hmz[a] − B*57 | 6.7 (1) | 4.7 (4) | 3.0 (3) | 0.378 |
| P*0102/*0202 | +Hmz[b] at A, B, or both | 6.7 (1) | 7.0 (6) | 3.0 (3) | 0.250 |
|  | +Htr[b] at A, B, or both | 20.0 (3) | 11.6 (10) | 8.0 (8) | 0.155 |
|  | +B*57 | 0 | 3.5 (3) | 2.0 (2) | 0.934 |
|  | −B*57 | 26.7 (4) | 15.1 (13) | 9.0 (9) | 0.045 |
|  | −Hmz[a] − B*57 | 20.0 (3) | 10.5 (9) | 6.0 (6) | 0.070 |

[a] 1 + 2 = P*0101/*0201 and P*0101/*0202, both involving the 59029G-carrying P*0101.
[b] Hmz, homozygosity; Htr, heterozygosity.

EXAMPLE 13

Mediation of HIV-1 Infection by CCR5 Promoter Genotypes is Independent of Effects by Non-genetic Factors Age, ethnicity and sexual and drug-using habits usually alter the risk of acquiring HIV-1 infection. For example, among heterosexual women in Kigali, the observed high risk factors included: 1) currently living alone but having multiple sexual partners or currently living with a single partner but both partners having extra-marital affairs (OR=1.8, p=0.024); 2) history of sexually transmitted disease in the past five years (OR=1.5, p=0.022); 3) having multiple lifetime sexual partners (OR=1.7, p=0.004); and 4) no condom use during sexual intercourse in the last 2 years (OR=8.6, p=0.0001). Risk factor 1 was strongly correlated with risk factor 2 among the Rwandan women ($\chi^2$=20.3, p=0.001).

Accordingly, the more strongly related risk factor 2 was chosen for additional analyses. For injecting drug users in New York, high risk factors included: 1) having sex with IV drug users (OR=2.6, p=0.039); 2) sharing needles in shooting galleries (OR=1.3, p=0.006); 3) attending shooting galleries (OR=1.5, p=0.065); and 4) sharing needles with strangers (OR=1.01, p=0.052).

Univariate analysis revealed that patterns of behavior (with regard to sex in Kigali and both sex and drug injection in New York) represented the strongest risk of getting infected. An ordinal scoring scheme summarizing these behavioral factors demonstrated a strong association with risk in the Kigali, but not in the New York cohort, suggesting that the latter group was strongly biased as a result of selective enrollment. Stratification of subjects by behavioral risk score revealed that CCR5 promoter allele P*0201 conferred more stable protection on subjects with the lowest risk score than on those with higher scores in Kigali (high risk OR=0.4, 95% CI=0.0–7.2; low risk OR=0.4, 95% CI=0.2–0.7). In contrast, individuals with intermediate to higher risk scores were better protected by P*0201 in New York (high risk OR=0.7–0.9; low risk OR=0.3–0.6) (Table 11). The risk associated with P*0101/*0101 genotype diminished in the New York cohort.

To assess the simultaneous and independent genetic and non-genetic effects, variables for age, behavioral risk, ethnicity and the two contributing CCR5 promoter genotypes (P*0101/P*0101 and P*0201) were incorporated into logistic regression analyses performed on separate data from Kigali and New York populations (Table 11). Age and risk score consistently served as independent determinants of HIV-1 infection in both cohorts. In Kigali, CCR5 promoter genotypes involving P*0201 were associated with decreased risk; in New York, the P*0101/*0101 genotype was associated with increased risk. Modest and inconsistent interaction between age and risk score and between ethnicity and CCR5 promoter variants did not contribute significantly to risk in the regression model. The two genotypes associated with contrasting outcomes of infection in the two cohorts are mutually exclusive of each other (Table 3), and their reciprocal effects are in agreement with apparent differences in their frequencies in the two populations (FIG. 4). Thus, it became evident that associations of the two promoter genotypes P*0101/P*0101 and P*0201 with higher and lower risk of HIV-1 infection, respectively, were independent of the effects of demographic and behavioral factors.

TABLE 11

Univariate and multivariate regression analyses showing the independent and relative contribution to HIV-1 infection by genetic and non-genetic factors in two cohorts

| Factors considered | OR (95% CI) | p |
|---|---|---|
| I. Logistic model for univariate analyses of the New York data set | | |
| Having sex with IV drug user | 2.6 (1.0–6.3) | 0.039 |
| Sharing needles in shooting galleries | 1.3 (1.1–1.6) | 0.006 |
| Attending shooting galleries | 1.5 (1.0–2.4) | 0.065 |
| Sharing needles with strangers | 1.0 (1.0–1.0) | 0.052 |

TABLE 11-continued

Univariate and multivariate regression analyses showing the independent and relative contribution to HIV-1 infection by genetic and non-genetic factors in two cohorts

| Factors considered | OR (95% CI) | p |
|---|---|---|
| Age | 0.9 (0.9–0.9) | 0.005 |
| Ethnicity | | |
| Caucasian Americans | 0.6 (0.3–1.1) | 0.110 |
| African Americans | 0.8 (0.4–1.8) | 0.609 |
| Hispanics | 1.7 (1.0–2.9) | 0.073 |
| CCR2b-64I | 0.9 (0.5–1.7) | 0.840 |
| CCR5-D32 | 1.7 (0.5–5.3) | 0.390 |
| CCR5 promoter P*0101/*0101 | 3.6 (1.5–8.4) | 0.004 |
| CCR5 promoter P*0201 | 0.5 (0.3–0.9) | 0.020 |
| SDF1-3'A | 1.5 (0.8–2.8) | 0.173 |
| II. Multivariate analyses of the New York data set HIV-1 infection = 1.60 + 0.31 × (sharing needles) − 0.06 × age − 0.83 × (being white) + 1.41 × (CCR5 promoter P*0101/*0101) | | |
| Sharing needles | OR = 1.4, CI = 1.1–1.7, p = 0.003 | |
| Age | OR = 0.9, CI = 0.9–1.0, p = 0.014 | |
| Being white | OR = 0.4, CI = 0.2–0.9, p = 0.021 |  |
| CCR5 P*0101/*0101 | OR = 4.1, CI = 1.7–10.2, p = 0.002 | |
| III. Logistic model for univariate analyses of the Kigali data set | | |
| Venereal disease in past 5 years | 2.5 (1.2–5.1) | 0.016 |
| Condom use 2 yrs prior to seroconversion | 0.02 (0.0–0.1) | 0.000 |
| Number of lifetime sexual partners | 1.5 (1.09–2.0) | 0.011 |
| Age | 0.9 (0.83–0.9) | 0.000 |
| CCR2b-64I | 1.6 (0.91–2.6) | 0.108 |
| CCR5 promoter P*0101/*0101 | 999.0 (0–0.900 999.0) | |
| CCR5 promoter P*0201 | 0.4 (0.3–0.7) | 0.001 |
| SDF1-3'A | 1.35 (0.65–2.81) | 0.417 |
| IV. Multivariate analyses of the Kigali data set HIV-1 infection = 7.36 + 1.18 × (venereal disease) − 4.54 × (condom use) − 0.09 × age − 0.87 (all CCR5 promoter genotypes involving P*0201) | | |
| Venereal disease in past 5 years | OR = 3.2, CI = 1.4–7.7, p = 0.007 | |
| Condom use 2 yrs prior to seroconversion | OR = 0.02, CI = 0.0–0.1, p = 0.000 | |
| Age | OR = 0.9, CI = 0.8–1.0, p = 0.024 | |
| CCR5 promoter P*0201 | OR = 0.4, CI = 0.2–0.8, p = 0.011 | |

EXAMPLE 14

The Observed Relationships Between CCR5 Promoter Polymorphisms and HIV-1 Infection Differed from the Previously Recognized Associations To compare previously reported relationships of CCR5 promoter sequences to progression with their relationships to infection seen here, the CCR5 promoter alleles were further aggregated into groups as defined by earlier methods. The effects of the P*0202-linked CCR2b-64I variant were also tested. By this reanalysis, the 59029G/G variant previously associated with slower disease progression and the P1/P1 genotype previously associated with faster disease progression separated mutually exclusive subsets of the promoter genotypes, explaining their opposing effects.

However, the previously recognized relationships between these two CCR5 promoter variants and HIV-1 disease progression almost contradicted their relationships to infection. For example, the 59029G/G (= all combinations involving only P*0101, P*0102, P*0103, and P*0104) was previously associated with slower disease progression (5). In the population cohorts described herein, P*0101/P*0101 (a subset of 59029G/G) showed unequivocal relationship to increased risk of infection (Table 8). Here, differences in population allele frequencies are unlikely to be a sufficient explanation.

The effects of the P1/P1 genotype differed even between the two cohorts: in Kigali, the P1/P1 genotype was associated with becoming infected, whereas in New York, the same genotype was associated with remaining uninfected. The effects of CCR2b-64I were the least stable when the 4 ethnic groups were analyzed separately. These apparently self-contradictory results contrast starkly with the strength and consistency of the relationships established by the typing scheme used herein, which had a definitive resolution of the promoter genotypes (Table 3). Thus, the manisfestation of CCR relationships appeared to be sensitive to ethnicity and allele definitions.

Summary

Intensive effort has been devoted to measuring the influence of polymorphisms in CCR5 and its promoter on the rates of disease progression during HIV-1 infection. The almost complete absence of HIV-1 infection in CCR5-Δ32 homozygotes has highlighted the importance of this co-receptor for initial penetration by the virus. It is conceivable that reduced production of CCR5 mediated by the promoter genotypes (5) can further determine the infectability by HIV-1. This aspect has heretofore escaped much of the attention surrounding the CCR5 promoter polymorphisms.

Based on earlier data derived from various ethnic groups, the four disease-related promoter alleles P*0101, P*0102, P*0201 and P*0202 differ in their frequencies in different populations. In particular, the promoter allele P*0201 occurs more frequently in Caucasoids (Caucasians and Hispanics, 34%) than in populations of African origin (22%). If the P*0201/*0201 (a subset of P1/P1) truly mediates more rapid progression to disease following HIV-1 infection, then a higher proportion of rapid progressors can be attributed to this genotype in Caucasians (11–12%) than Africans (4–5%). It would, therefore, be more difficult to detect the effect of P*0201/*0201 or P1/P1 genotype in populations of African origin. The lack of association between P1/P1 and rapid disease progression in African-Americans (6) reflects this difficulty, but a better resolution of the P1/P1 genotype is likely to pinpoit the exact alleles involved.

Despite the consistent associations between CCR5 promoter variants and contrasting rates of HIV-1 disease progression, the mechanisms for these effects are still puzzling. For example, none of the polymorphic promoter sites map within any of the 6 putative transcription factor-binding (TFB) elements (13,14), suggesting that other unknown neighboring factors in linkage disequilibrium are probably involved.

In summary, the work described herein confirmed the association of CCR5 genotype P1/P1 and further indicated that only the subset represented by the P*0201/*0201 genotype was the true factor in the Rwandan populatrion studied. Meanwhile, two promoter genotypes, P*0101/*0201 and P*0101/*0202, collectively and individually showed the opposite effects. The appearance and strength of the association of CCR2b-64I obviously depended on the relative frequencies of 2 competing CCR5 promoter genotypes, P*0102/*0202 and P*0201/*0202, both involving the CCR2b-64I-carrying P*0202 allele. In addition, the disease-accelerating effect of P*0201/*0201 is predicted to be more significant to Caucasian and Hispanic populations, whose P*0201 frequencies are higher than those of populations of African origin.

The consistent effects associated with CCR5 promoter alleles in ethnically diverse populations studied herein are less dramatic compared with those associated with CCR5-Δ32 and CCR5-m303. It is unlikely that a simple mechanism can explain all of the observed relationships. The exisitng data pool already points to a complex phenomenon that depends on a combination of differences in promoter activities (5), in splicing of CCR5 transcription products (13), and in the relative prevalence of M- and T-tropic quasispecies at different stages of HIV-1 infection (40,55). There is also limited evidence that the co-receptor usage by HIV-1 may be governed not only by CCR5 expression (37,52), but also by the ratio between CCR5 coreceptor and $CD4^+$ on the cell surface (19). If the relative expression of CCR5 and $CD4^+$ is altered after infection, the effects exerted by a promoter genotype at the inception of HIV-1 infection could appear very different from those seen at later stages.

There are three single nucleotide changes between the promoter alleles P*0101 and P*0201, however none of them occur in any of the six putative transcription factor-binding elements. If the different effects associated with these two alleles have anything to d o with differential transcription of CCR5, there are probably additional unrecognized elements in the promoter region. Meanwhile, two of the three nucleotide changes between CCR5 promoter alleles P*0101 and P*0201 are located in the untranslated region (exon 1) of CCR5 mRNA. These sites (59353 and 59402) may alter the translation rather than transcription. The relatively high frequency of promoter alleles P*0101 and P*0201 in different ethnic groups suggested that these factors can be more significant than the two Caucasian-specific factors in the CCR5 locus previously shown to mediate HIV-1 transmission.

TABLE 12

Allele assignment for CCR2b, CCR5 and CCR5 promoter alleles based upon PCR-SSP

| Genotypes | DNA band(s) visualized in SSP reaction | Notes |
| --- | --- | --- |
| CCR2b-64V | 1a = 413 bp (++++) | RFLP applicable (Smith, 1997) |
| CCR2b-64I | 1b = 413 bp (++++) | 1b always has 4b = 309 bp (++++) |
| CCR5 wild type | 1b = 585 bp (+++) | 197 bp control product |
| CCR5-Δ32 | 1b = 553 bp (+++) | 165 bp control product |
| P*0101 | 2a = 363 bp (++++); 3a = 412 bp (++++); 4a = 309 bp (++++) | extra 5a = 367 bp (++++) |

TABLE 12-continued

Allele assignment for CCR2b, CCR5 and CCR5 promoter alleles based upon PCR-SSP

| Genotypes | DNA band(s) visualized in SSP reaction | Notes |
|---|---|---|
| P*0102 | 2a = 363 bp (++++); <br> 3b = 412 bp (++++); <br> 4a = 309 bp (++++) | extra 5a = 367 bp (++++) |
| P*0103 | 2a = 363 bp (+/−); <br> 3b = 412 bp (++++); <br> 4a = 309 bp (++++) | extra 2e = 363 bp (++++), <br> 5b = 367 bp (++++) |
| P*0201 | 2d = 363 bp (++++); <br> 3d = 412 bp (++++); <br> 4a = 309 bp (++++) | 5b = 367 bp (++++) <br> NA |
| P*0202 | 2d = 363 bp (++++); <br> 3d = 412 bp (++++); <br> 4b = 309 bp (+++) | 4b (+++) usually has <br> 1b = 413 bp (++++) |

Figure 2:
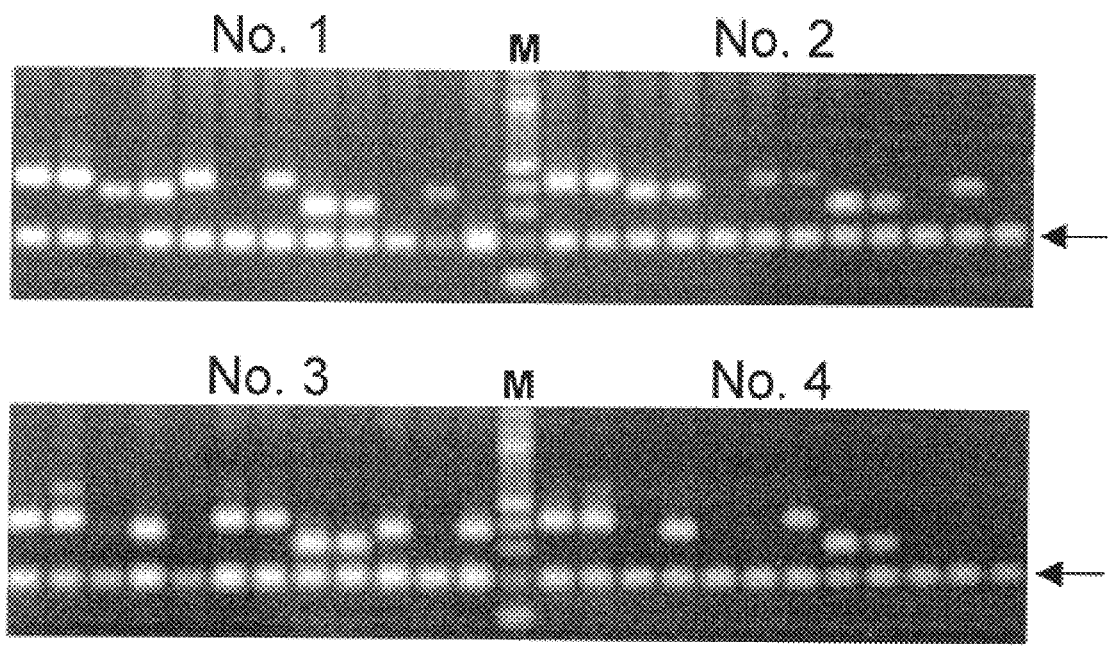
FIG. 2 shows examples of PCR-SSP-based typing of CCR5 variants. Four samples (No. 1 to No. 4) are shown with 12 selected SSP reactions (1a, 1b, 2a, 2d, 3a, 3b, 3d, 4a, 4b, 2e, 5a, 5b (from left to right)). Arrows indicate the position of the control product that is present in all reactions. DNA size markers (M) (New England Biolabs) are also included. Sample No. 1 has the genotype CCR5 wild type WT/WT, CCR2b-64V/1 and CCR5 promoter P*0101/P*0202; Sample No. 2 has the genotype CCR5 WT/WT, CCR2b-64V/I and CCR5 promoter P*0102/P*0202; Sample No. 3 has the genotype CCR5 WT/WT, CCR2b-64V/I and CCR5 promoter P*0103/P*0202; Sample No. 4 has the genotype CCR5 WT/WT, CCR2b-64V/1 and CCR5 promoter P*0201/P*0202.

The intensity of specific products is measured as: ++++ very strong; +++ strong; ++ clearly visible; + weak; +/− weak or invisible. See also FIG. 2.

EXAMPLE 15

Figure 7:
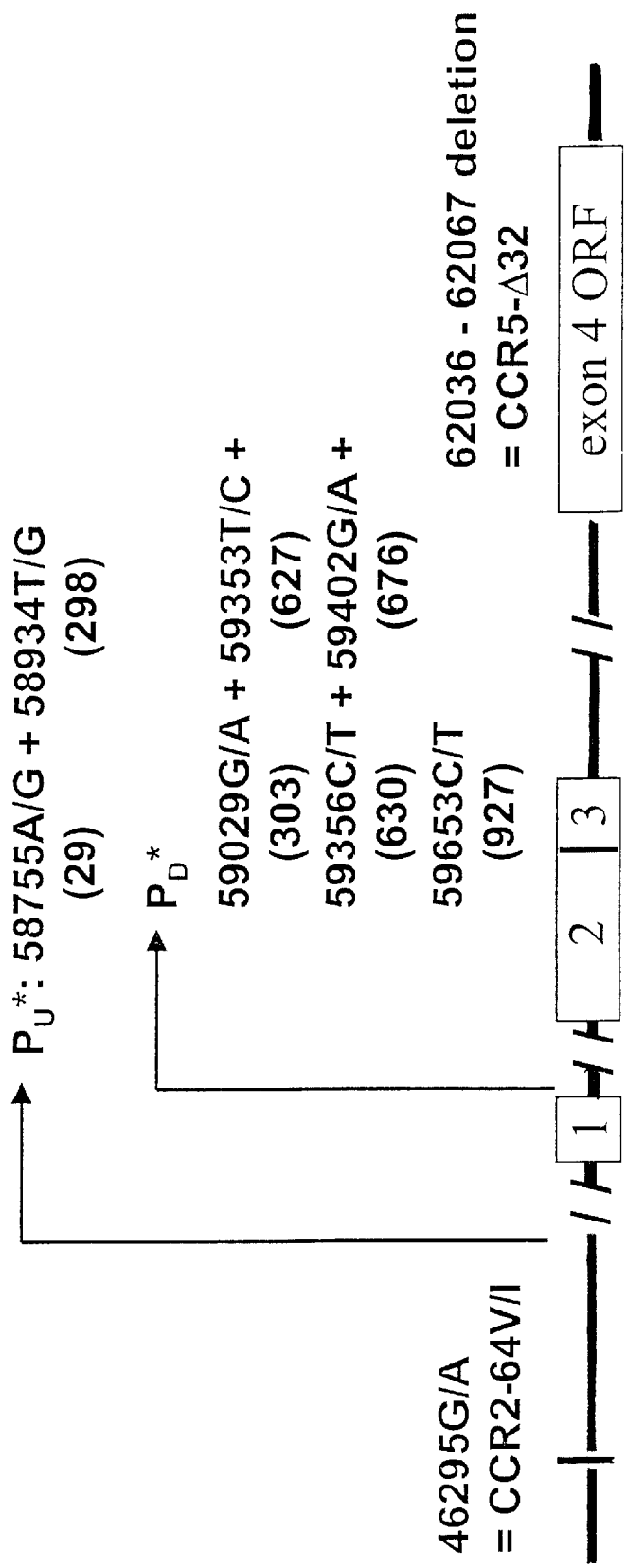
FIG. 7 shows polymorphic sites at the CCR2 and CCR5 loci. Nomenclature for the CCR5 upstream ($P_u$) and downstream ($P_D$) sequence differs widely among studies. The alternative numbering of nucleotides is given in parentheses.
Figure 8:
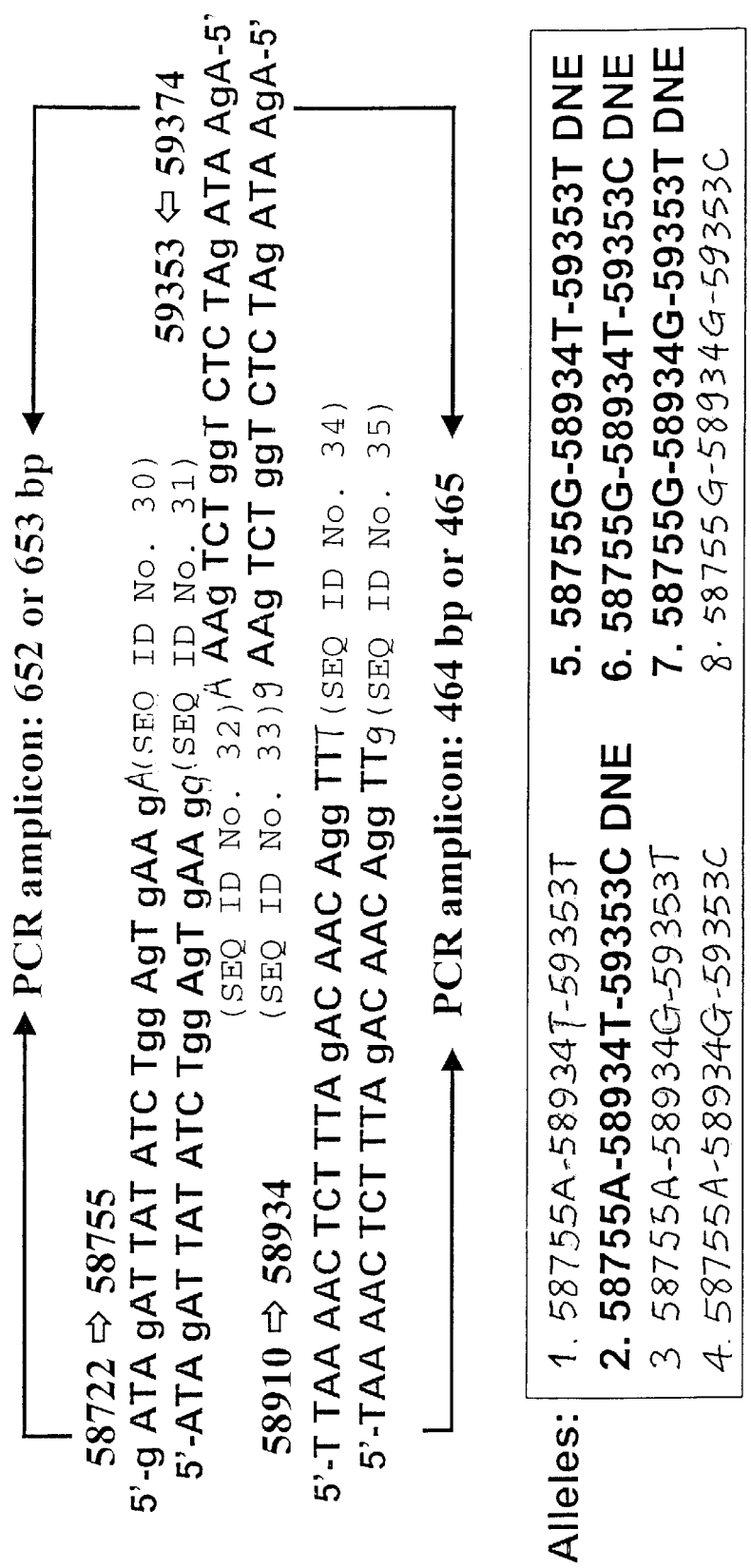
FIG. 8 shows PCR haplotyping of CCR5 upstream promoter variants using sequence-specific primers.
Figure 10A:
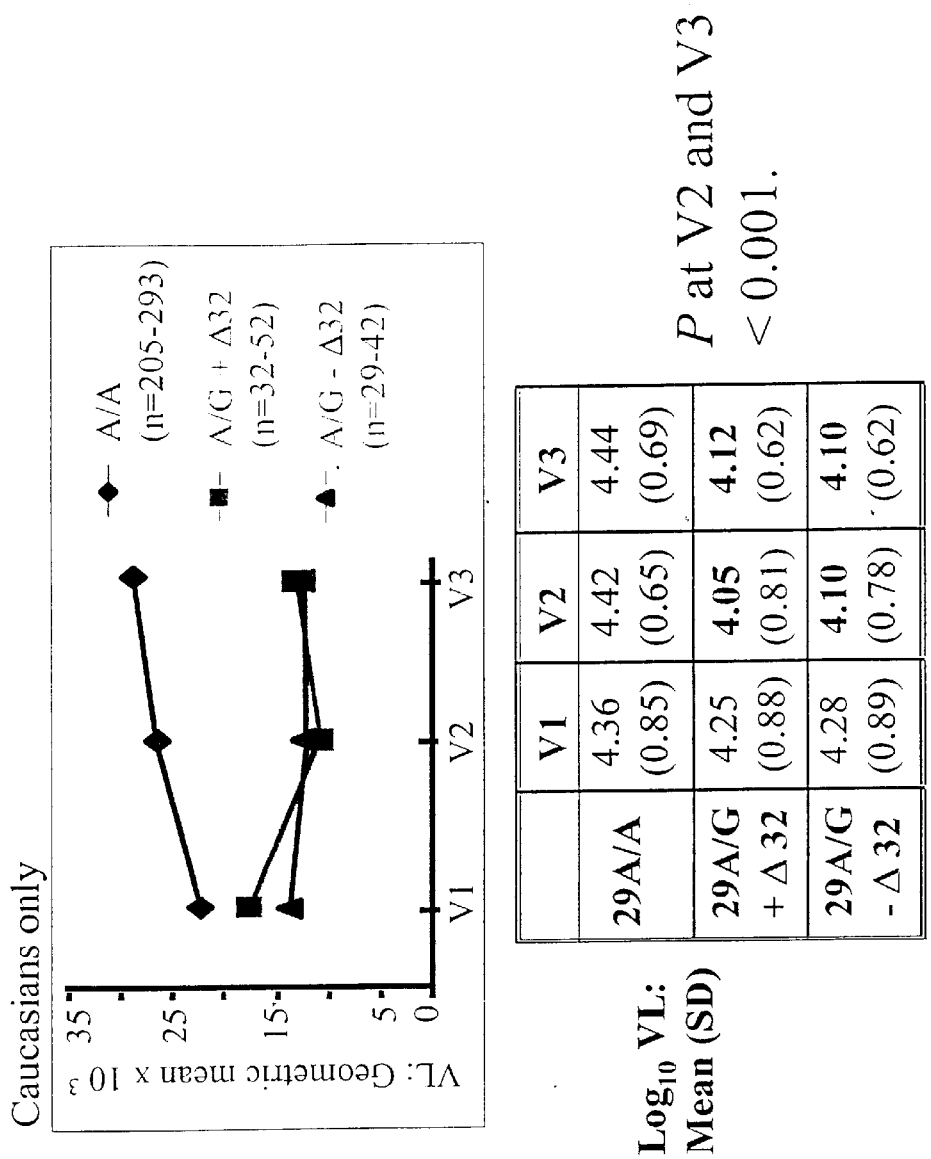
FIG. 10A shows VL according to $P_u$ 58755 (29) A/G and the linked CCRS-Δ32.
Figure 10B:
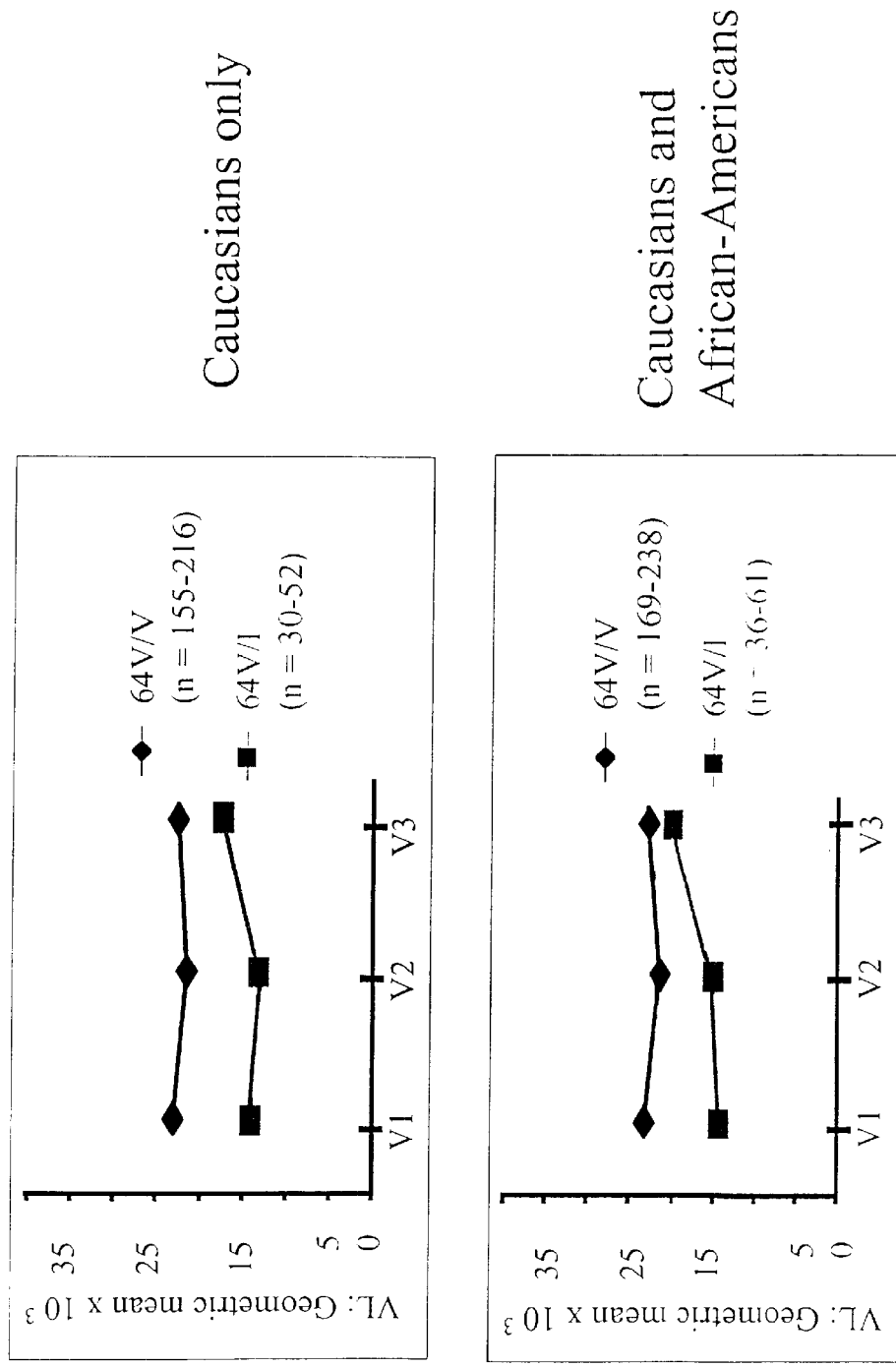
FIG. 10B shows VL according to CCR2-64V/I. V1, V2 and V3 were three different visits.
Figure 13:
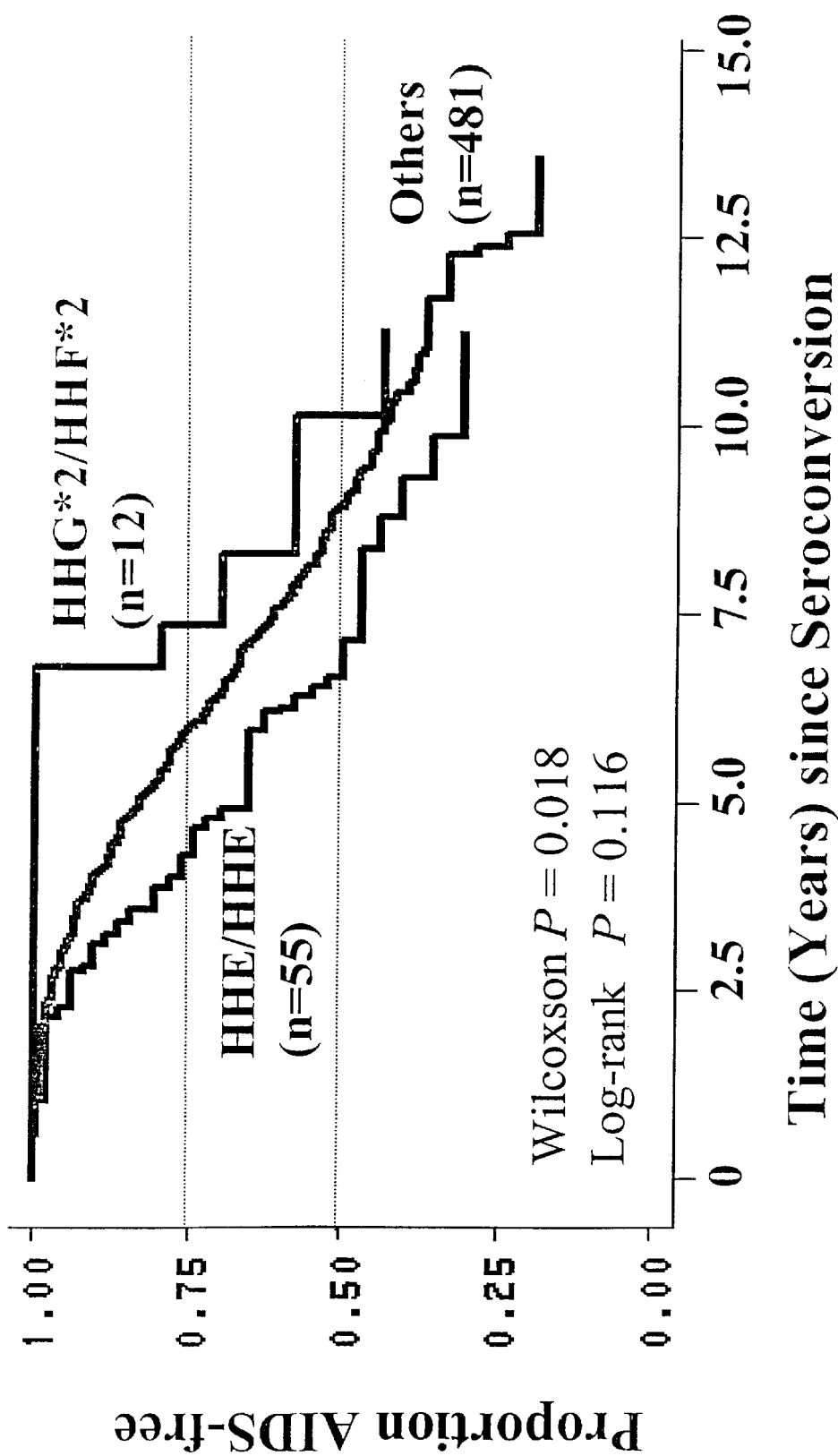
FIG. 13 shows the relationship between CCR5 genotypes and disease progression.

CCR5 Genotypes Determine Progression of HIV-1 Infection by Regulating Early Viral Load Up to 306 mostly caucasians homosexual HIV-1 seroconverters from the Multicenter AIDS Cohort Studies and District of Columbia Gay Cohort had viral load (VL) measurements 6–36 months after seroconversion. Men were typed by multiplexing PCR with sequence-specific primers that simultaneously defined markers such as: CCR2b-64I and cis-regulatory dimorphisms G303A, T627C, C630T, A676G, C927T (including the P1/P1 pairing reported in association with rapid progression), and A32 in CCR5 (FIG. 7). Viral load (Chiron or Roche) was reported as $\log_{10}$. The GLM procedure in SAS was used to model the relationships.

Age-, race-, cohort-adjusted mean VL at a median of about 15 months was 4.33. Overall Δ32 carriers showed clearly lower VL (4.06, p=0.008), 64I showed only a modest reduction (VL=4.21) and P1/P1 showed no reduction (VL=4.38). In a multivariate model, compared with the reference group (n=224), men who carried Δ32 in the absence of the homozygous A-C-C-A-C haplotype (a subset of P1/P1) had lower VL both in the presence (3.38, p=0.03) and the absence (4.01, p=0.001) of the 64I-linked A-C-C-A-C haplotype. Conversely, men who carried the homozygous A-C-C-A-C haplotype in the absence of Δ32 had higher VL (4.52, p=0.05). The overall adjusted model for association of CCR genotypes with VL was highly predictive (p=0.0005).

CCR5 genotype HHE/HHE (FIG. 9) contributed the majority of effect on VL and disease progression, causing >2-year acceleration to the onset of AIDS in 10% of the participants. The infrequent CCR5 genotype carrying Δ32 (HHG*2) and 64I (HHF*2) had a strong protective effect (lower VL and longer time to AIDS) in 2% of the participants. CCR2-64I alone conferred slight but not significant protection against HIV-1 VL or disease progression.

In conclusion, comprehensive genotyping of CCR2b and CCR5 regulatory and coding region variants coupled with analysis accounting for linkage disequilibria between the variants indicated that Δ32, the 64I-linked A-C-C-A-T CCR5 promoter haplotype, and the homozygous A-C-C-A-C genotype collectively determine later disease progression partly by governing viral load early in infection.

The following references were cited herein:
1. Dean M, et al. *Science* 1996; 273: 1856–1862.
2. Kostrikis L G, et al. *Nature Med* 1998; 4: 350–353.
3. Mummidi S, et al. *Nature Med* 1998; 4: 786–793.
4. Smith M W, et al. *Science* 1997; 277: 959–965.
5. McDermott D H, et al. *Lancet* 1998; 352: 866–870.
6. Martin M P, et al. *Science* 1998; 282: 1907–1911.
7. Fauci A S. *Nature* 1996; 384: 529–534.
8. Chen J-D, et al. *Nature Med* 1997; 3: 1110–1116.
9. Simmons G, et al. *Science* 1997; 276: 276–279.
10. Michael N L, et al. Nature Med 1997; 3: 1160–1162.
11. loannidis J P A, et al. *Nature Med* 1998; 4: 536.
12. Garred P. *Lancet* 1998; 351: 2–3.
13. Mummidi S, et al. *J Biol Chem* 1997; 272: 30662–30671.
14. Guignard F, et al. *J Immunol* 1998; 160: 985–992.
15. Mindell D P, et al. *Syst Biol* 1995; 44: 77–92.
16. Gao F, et al. *Nature* 1999; 397: 436–441.
17. Chen Z, et al. *J Virol* 1997; 71: 2705–2714.
18. Hoffman & Doms, *AIDS* 1998; 12 (suppl A): S17-S26.
19. Ward S G, et al. *Immunity* 1998; 9: 1–11.
20. Lindan C P, et al. *Ann Intern Med* 1992; 116: 320–328.
21. Lifson A R, et al. *Ann Intern Med* 1995; 122: 262–270.
22. Gourevitch M N, et al. *N Engl J Med* 1995; 332: 1170.
23. Hartel, et al. *Pub Health Rep* 1998; 113 (1): 107–115.
24. Miller S A, et al. *Nucl Acids Res* 1988; 16: 1215.
25. Grimberg J, et al. *Nucl Acids Res* 1989; 17: 8390.
26. Tang J & Unnasch T R. *BioTechniques* 1995; 19: 902–905.
27. Klitz W, et al. *Am J Hum Genet* 1995; 57: 1436–1444.
28. Ronningen K S, et al. *J Immunol* 1993; 23: 1050–1056.
29. Felsenstein J. PHYLIP (Phylogeny Inference Package). Department of Genetics, University of Washington: Seattle, Wash., 1993.
30. Sworford DL. PAUP. Ilinois Natural History Survey: Champaign, Ill., 1991.
31. Kimura M. *J Mol Evol* 1980; 16: 111–120.
32. Saitou, et al. *Molecular Biology and Evolution* 1987; 4: 406–425.
33. Dean, A G, et al. Epi Info, Version 6: A Word-Processing, Database, and Statistics Program for Public Health on IBM-Compatible Microcomputers. Atlanta, Ga.: Centers for Disease Control and Prevention; 1995.
34. Anzala, A O, et al. *Lancet* 1998, 351: 1632–1633.
35. Graziosi, C & Pantaleo, G *Nat Med* 1997, 3: 1318–1320.
36. Deng, H, et al. *Nature* 1996, 381: 661–666.
37. Zaitseva, M, et al. *Nature Med* 1997; 3: 1369–1375.
38. Doranz, B J, et al. *Cell* 1996, 85: 1149–1158.
39. Deng, HK, et al. *Nature* 1997; 388: 296–300.
40. Scalatti, G, et al. *Nature Med* 1997, 3: 1259–1265.
41. Huang, Y, et al. *Nature Med* 1996, 2: 1240–1243.
42. Liu, R, et al. *Cell* 1996, 86: 367–377.
43. Samson, M, et al. *Nature* 1996, 382: 722–725.
44. Zimmerman, P A, et al. *Mol Med* 1997; 3: 23–36.
45. Quillent, C, et al. *Lancet* 1998; 351: 14–18.
46. Eugen-Olsen, J, et al. *AIDS* 1997, 11: 305–310.
47. Benkirane, M, et al. *J Biol Chem* 1997; 272: 30603–30606.
48. Carrington, et al. *Am J Hum Genet* 1997, 61: 1261–1267.
49. Ansari-Lari, M A, et al. *Nat Genet* 1997, 16: 221–222.
50. Zhang, et al. *AIDS Res Hum Retroviruses* 1997, 13:1357–1366.
51. Paxton, W A, et al. *Nature Med* 1996, 2: 412–417.
52. Wu, L, et al. *J Exp Med* 1997, 185: 1681–1691.
53. Moriuchi, H, et al. *J Immunol* 1997, 159: 5441–5449.

54. Winkler, C, et al. *Science* 1998, 279: 389–93.
55. Glushakova, S, et al. *Nature Med* 1998, 4: 346–349.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of surveying CCR genotypes in a population, comprising the steps of:

(a) obtaining biological samples from a representative number of individuals in a population, wherein each sample is from a different individual, wherein said sample comprises genomic DNA;

(b) combining a portion of each sample with an experimental primer combination and a control primer combination, thereby producing primer-annealed DNA, wherein said experimental primer combination is SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein said control primer combination is SEQ ID Nos. 17 & 18;

(c) amplifying said primer-annealed DNA in a reaction, thereby producing amplicons, wherein reaction conditions for said amplification are optimized for sequence-specific amplification, wherein each experimental primer combination and said control primer combination are predicted to produce one or more amplicons having expected sizes in basepairs;

(d) separating said amplicons by size, wherein the presence of:

a 197 bp amplicon with said control primer combination is indicative of a CCR5 wildtype coding sequence;

a 165 bp amplicon with said control primer combination is indicative of a CCR5-Δ32 coding sequence;

a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12 and a 309 bp amplicon with experimental primer combination SEQ ID Nos. 14 & 16 is indicative of a P*0101 CCR5 promoter allele;

a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13 and a 309 bp amplicon with experimental primer combination SEQ ID Nos. 14 & 16 is indicative of a P*0102 CCR5 promoter allele;

a 363 bp amplicon with experimental primer combination SEQ ID Nos. 5 & 7, a 363 bp amplicon with experimental primer combination SEQ ID Nos. 5 & 9, a 367 bp amplicon with experimental primer combination SEQ ID Nos. 5 & 11, a 412 bp amplicon with experimental primer combination SEQ ID Nos. 5 & 13 and a 309 bp amplicon with experimental primer combination SEQ ID Nos. 14 & 16 is indicative of a P*0103 CCR5 promoter allele;

a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a P*0201 CCR5 promoter allele;

a 363 bp amplicon with experimental primer combination SEQ ID Nos. 6 & 8, a 412 bp amplicon with experimental primer combination SEQ ID Nos 6 & 13 and a 309 bp amplicon with experimental primer combination SEQ ID Nos. 15 & 16 is indicative of a P*0202 CCR5 promoter allele;

(e) determining a CCR genotype for each sample based upon said CCR alleles indicated following step (d), and (f) compiling said genotypes determined in step (e), thereby genotyping said representative number of individuals in said population, thereby surveying CCR genotypes in said population.

2. The method of claim 1, wherein said biological samples are selected from the group consisting of blood, serum, saliva, semen, tissue biopsy and DNA.

3. The method of claim 1, wherein said separation is selected from the group consisting of gel electrophoresis and size fractionation.

4. The method of claim 1, wherein said amplifying is by polymerase chain reaction (PCR).

5. A method of surveying HIV-1 co-receptor CCR alleles in an individual, comprising the steps of:
(a) obtaining a biological sample from an individual, wherein said sample comprises genomic DNA;
(b) combining a portion of said sample with an experimental primer combination and a control primer combination, thereby producing primer-annealed DNA, wherein said experimental primer combination is SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein said control primer combination is SEQ ID Nos. 17 & 18;
(c) amplifying said primer-annealed DNA in a reaction, thereby producing amplicons, wherein reaction conditions for said amplification are optimized for sequence-specific amplification, wherein each experimental primer combination and said control primer combination are predicted to produce one or more amplicons having expected sizes in basepairs; and
(d) separating said amplicons by size, wherein the presence of:
a 197 bp amplicon with said control primer combination is indicative of a CCR5 wildtype coding sequence;
a 165 bp amplicon with said control primer combination is indicative of a CCR5-Δ32 coding sequence;
a 363 bp amplicon with experimental primer combination SEQ ID Nos. 5 & 7, a 367 bp amplicon with experimental primer combination SEQ ID Nos, 5 & 10, a 412 bp amplicon with experimental primer combination SEQ ID Nos. 5 & 12 and a 309 bp amplicon with experimental primer combination SEQ ID Nos. 14 & 16 is indicative of a P*0101 CCR5 promoter allele;
a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13 and a 309 bp amplicon with experimental primer combination SEQ ID Nos. 14 & 16 is indicative of a P*0102 CCR5 promoter allele;
a 363 bp amplicon with experimental primer combination SEQ ID Nos. 5 & 7, a 363 bp amplicon with experimental primer combination SEQ ID Nos. 5 & 9, a 367 bp amplicon with experimental primer combination SEQ ID Nos. 5 & 11, a 412 bp amplicon with experimental primer combination SEQ ID Nos. 5 & 13 and a 309 bp amplicon with experimental primer combination SEQ ID Nos. 14 & 16 is indicative of a P*0103 CCR5 promoter allele;
a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a P*0201 CCR5 promoter allele;

a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 15 & 16 is indicative of a P*0202 CCR5 promoter allele.

6. The method of claim 5, wherein said biological samples are selected from the group consisting of blood, serum, saliva, semen, tissue biopsy and DNA.

7. The method of claim 5, wherein said separation is selected from the group consisting of gel electrophoresis and size fractionation.

8. The method of claim 5, wherein said amplifying is by polymerase chain reaction (PCR).

9. A method of predicting the disease progression of AIDS in an HIV-1-infected individual, comprising the steps of:
(a) obtaining a biological sample from an individual, wherein said sample comprises genornic DNA;
(b) combining a portion of said sample with an experimental primer combination and a control primer combination, thereby producing primer-annealed DNA, wherein said experimental primer combination is SEQ ID Nos 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein said control primer combination is SEQ ID Nos. 17 & 18;
(c) amplifying said primer-annealed DNA in a reaction, thereby producing amplicons, wherein reaction conditions for said amplification are optimized for sequence-specific amplification, wherein each experimental primer combination and said control primer combination are predicted to produce one or more amplicons having expected sizes in basepairs;
(d) separating said amplicons by size, wherein the presence of:
a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a CCR5 promoter genotype of P*0201/P*0201;
a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13, a 363 bp amplicon with experimental primer combination SEQ ID Nos. 6 & 8, a 412 bp amplicon with experimental primer combination SEQ ID Nos. 6 & 13, a 309 bp amplicon with experimental primer combination SEQ ID Nos. 14 & 16 and a 309 bp amplicon with experimental primer combination SEQ ID Nos. 15 & 16 is indicative of a CCR5 promoter genotype of P*0102/P*0202;
a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12, a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a CCR5 promoter genotype of P*0101/P*0201;
a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12, a 363 bp amplicon with experimental primer combination SEQ ID Nos. 6 & 8, a 412 bp amplicon with experimental primer combination SEQ ID Nos. 6 & 13, a 309 bp amplicon with experimental primer combination SEQ ID Nos. 14 & 16 and a 309 bp amplicon with experimental primer combination SEQ ID Nos. 15 & 16 is indicative of a CCR5 promoter genotype of P*0101/P*0202;

wherein a CCR5 promoter genotype of P*0201/P*0201 or P*0102/P*0202 is predictive of an accelerated rate of AIDS progression in said individual relative to an individual who does not possess said P*0201/P*0201 or P*0102/P*0202 gentoype, wherein a CCR5 promoter genotype of P*O101/P*0201 or P*0101/P*0202 is predictive of a slower rate of AIDS progression in said individual relative to an individual who does not possess said P*0101/P*0201 or P*0101/P*0202 gentoype.

10. The method of claim 9, wherein said biological samples are selected from the group consisting of blood, serum, saliva, semen, tissue biopsy and DNA.

11. The method of claim 9, wherein said separation is selected from the group consisting of gel electrophoresis and size fractionation.

12. The method of claim 9, wherein said amplifying is by polymerase chain reaction (PCR).

13. A method of predicting the probability of HIV-1 infection in an individual, comprising the steps of:
(a) obtaining a biological sample from an individual, wherein said sample comprises genomic DNA;
(b) combining a portion of said sample with an experimental primer combination and a control primer combination, thereby producing primer-annealed DNA, wherein said experimental primer combination is SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein said control primer combination is SEQ ID Nos. 17 & 18:
(c) amplifying said primer-annealed DNA in a reaction, thereby producing amplicons, wherein reaction conditions for said amplification are optimized for sequence-specific amplification, wherein each experimental primer combination and said control primer combination are predicted to produce one or more amplicons having expected sizes in basepairs; and
(d) separating said amplicons by size, wherein the presence of:
a 363 bp with experimental primer combination SEQ ID Nos. 6 & 8, a 412 bp with experimental primer combination SEQ ID Nos. 6 & 13 and a 309 with experimental primer combinations SEQ ID Nos. 14 & 16 is indicative of a CCR5 promoter genotype P*0201/P*0201;
a 363 bp with experimental primer combination SEQ ID Nos. 5 & 7, a 367 bp with experimental primer combination SEQ ID Nos. 5 & 10, a 412 bp with experimental primer combination SEQ ID Nos. 5 & 12 and a 309 bp with experimental primer combination SEQ ID Nos. 14 & 16 is indicative of a CCR5 promoter genotype of P*0101/P*0101;
wherein a CCR5 promoter genotype of P*02011/P*0201 is predictive of a decreased probability of HIV-1 infection in said individual relative to an individual who does not possess said P*0201/P*0201 genotype, wherein a CCR5 promoter genotype of P*0101/P*0101 is predictive of an increased probability of HIV-1 infection in said individual relative to an individual who does not possess said P*0101/P*0101 genotype.

14. The method of claim 13, wherein said biological samples are selected from the group consisting of blood, serum, saliva, semen, tissue biopsy and DNA.

15. The method of claim 13, wherein said separation is selected from the group consisting of gel electrophoresis and size fractionation.

16. The method of claim 13, wherein said amplifying is by polymerase chain reaction (PCR).

17. A method of correlating CCR genotypes with HIV-1 ssion and/or disease progression, comprising the steps of:
(a) obtaining biological samples from a representative of individuals, wherein each sample is from a different individual, said sample comprises genomic DNA;
(b) assessing each individual's HIV-1 status and/or risk of acquiring HIV-1;
(c) assigning each individual to a risk group, wherein said assignment is based upon said individual's HIV-1 status and/or risk of acquiring HIV-1;
(d) combining a portion of each sample with an experimental primer combination and a control primer combination, thereby producing primer-annealed DNA, wherein said experimental primer combination is SEQ ID Nos. 2 & 3, 2 & 4, 5 & 7, 5 & 8, 5 & 9, 5 & 10, 5 & 11, 5 & 12, 5 & 13, 6 & 7, 6 & 8, 6 & 12, 6 & 13, 14 & 16 and 15 & 16, wherein said control primer combination is SEQ ID Nos. 17 & 18;
(e) amplifying said primer-annealed DNA in a reaction, thereby producing amplicons, wherein reaction conditions for said amplification are optimized for sequence-specific amplification, wherein each experimental primer combination and said control primer combination are predicted to produce one or more amplicons having expected sizes in basepairs; and
(f) separating said amplicons by size, wherein the presence of:
a 197 bp amplicon with said control primer combination is indicative of a CCR5 wildtype coding sequence;
a 165 bp amplicon with said control primer combination is indicative of a CCR5-Δ32 coding sequence;
a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 12 and a 309 bp amplicon with experimental primer combination SEQ ID Nos. 14 & 16 is indicative of a P*0101 CCR5 promoter allele;
a 363 bp amplicon with experimental primer combination SEQ ID Nos. 5 & 7, a 367 bp amplicon with experimental primer combination SEQ ID Nos. 5 & 10, a 412 bp amplicon with experimental primer combination SEQ ID Nos. 5 & 13 and a 309 bp amplicon with experimental primer combination SEQ ID Nos. 14 & 16 is indicative of a P*0102 CCR5 promoter allele;
a 363 bp amplicon with experimental primer combination SEQ ID Nos. 5 & 7, a 363 bp amplicon with experimental primer combination ID Nos. 5 & 9, a 367 bp amplicon with experimental primer combination SEQ ID Nos. 5 & 11, a 412 bp amplicon with experimental primer combination SEQ ID Nos. 5 & 13 and a 309 bp amplicon with experimental primer combination SEQ ID Nos. 14 & 16 is indicative of a P*0103 CCR5 promoter allele;

a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 14 & 16 is indicative of a P*0201 CCR5 promoter allele;

a 363 bp amplicon with experimental primer combination SEQ ID Nos. 6 & 8, a 412 bp amplicon with experimental primer combination SEQ ID Nos. 6 & 13 and a 309 bp amplicon with experimental primer combination SEQ ID Nos. 15 & 16 is indicative of a P*0202 CCR5 promoter allele;

(g) determining a CCR genotype for each sample based upon said CCR alleles indicated following step (f); and (h) analyzing said genotypes determined in step (g), thereby genotyping said representative number of individuals with respect to said risk group assigned each individual, thereby correlating CCR genotypes with HIV-1 transmission and/or disease progression.

18. The method of claim 17, wherein said biological samples are selected from the group consisting of blood, serum, saliva, semen, tissue biopsy and DNA.

19. The method of claim 17, wherein said separation is selected from the group consisting of gel electrophoresis and size fractionation.

20. The method of claim 17, wherein said amplifying is by polymerase chain reaction (PCR).

21. The method of claim 17, wherein said analyzing is by means selected from the group consisting of two-tailed Fisher's exact test, multiple logistic regression analysis, univariate analysis and multivariate analyses.

* * * * *